US007611720B2

(12) United States Patent
Liu et al.

(10) Patent No.: US 7,611,720 B2
(45) Date of Patent: Nov. 3, 2009

(54) TUBERCULOSIS VACCINES INCLUDING RECOMBINANT BCG STRAINS EXPRESSING ALANINE DEHYDROGENASE, SERINE DEHYDRATASE AND/OR GLUTAMINE SYNTHETASE

(75) Inventors: Jun Liu, Faculty of Medicine, University of Toronto, Dept. Medical Genetics and Microbiology, Medical Sciences Building, 1 Kings College Circle, Rm. 4382, Toronto, Ontario (CA) M5S 1A8; Jeffrey Chen, Toronto (CA); David Alexander, Toronto (CA)

(73) Assignee: Jun Liu, Toronto (CA)

( * ) Notice: Subject to any disclaimer, the term of this patent is extended or adjusted under 35 U.S.C. 154(b) by 33 days.

(21) Appl. No.: 10/511,718

(22) PCT Filed: Apr. 16, 2003

(86) PCT No.: PCT/CA03/00566

§ 371 (c)(1),
(2), (4) Date: Jul. 28, 2006

(87) PCT Pub. No.: WO03/089462

PCT Pub. Date: Oct. 30, 2003

(65) Prior Publication Data

US 2007/0264286 A1    Nov. 15, 2007

Related U.S. Application Data

(60) Provisional application No. 60/372,450, filed on Apr. 16, 2002.

(51) Int. Cl.
*A61K 39/04* (2006.01)
*A61K 49/00* (2006.01)
*A61K 39/00* (2006.01)

(52) U.S. Cl. .............. 424/248.1; 536/23.1; 536/23.7; 530/300; 530/350; 424/9.1; 424/9.2; 424/185.1; 424/190.1; 424/243.1; 435/7.1; 435/7.2

(58) Field of Classification Search ............... 424/9.1, 424/9.2, 185.1, 190.1, 243.1, 248.1; 435/7.1, 435/7.2; 530/300, 350; 536/23.1, 23.7
See application file for complete search history.

(56) References Cited

FOREIGN PATENT DOCUMENTS

| WO | WO 00/11214 A | 3/2000 |
| WO | WO 01/078774 A | 10/2001 |

OTHER PUBLICATIONS

TB Vaccines: Progress and Problems; Trends in Immunology, vol. 22, Issue 3, dated Mar. 1, 2001, pp. 160-168.
Long-Term Maintenance Bacille Calmette-Guerin Therapy in High-Grade Superficial Bladder Cancer; Urology, vol. 59, Issue 3, dated Mar. 2002, pp. 414-418.
Glutamine Synthetase of *Mycobacterium tuberculosis*: Extracellular Release and Characterization of its Enzymatic Activity; Proc. Natl. Acad. Sci. USA, vol. 91, dated Sep. 1994, pp. 9342-9346.
An Inhibitor of Exported *Mycobacterium tuberculosis* Glutamine Synthetase Selectively Blocks the Growth of Pathogenic Mycobacteria in Axenic Culture and in Human Monocytes: Extracellular Proteins as Potential Novel Drug Targets; Department of Medicine, University of California at Los Angeles School of Medicine, vol. 189, No. 9, dated May 3, 1999, pp. 1425-1435.
*Mycobacterium bovis* BCG Vaccines Exhibit Defects in Alanine and Serine Catabolism; Infection and Immunity, Feb. 2003, pp. 708-716.

*Primary Examiner*—Rodney P. Swartz

(57) ABSTRACT

The invention relates to a live recombinant *Mycobacterium bovis*-BCG strain comprising a nucleic acid capable of expression, the nucleic acid encoding at least one protein or polypeptide that exhibits alanine dehydrogenase activity, glutamine synthetase activity, or serine dehydratase activity.

24 Claims, 9 Drawing Sheets

A

```
M.tb     ATG CGC GTC GGT ATT CCG ACC GAG ACC AAA AAC AAC GAA TTC CGG GTG GCC ATC
M.bovis  ATG CGC GTC GGT ATT CCG ACC GAG ACC AAA AAC AAC GAA TTC CGG GTG GCC ATC M.tb     ACC CCG GCC GGC GTC GCG GAA CTA ACC CGT CGT GGC CAT GAG GTG CTC ATC CAG
M.bovis  ACC CCG GCC GGC GTC GCG GAA CTA ACC CGT CGT GGC CAT GAG GTG CTC ATC CAG M.tb     GCA GGT GCC GGA GAG GGC TCG GCT ATC ACC GAC GCG GAT TTC AAG GCG GCA GGC
M.bovis  GCA GGT GCC GGA GAG GGC TCG GCT ATC ACC GAC GCG GAT TTC AAG GCG GCA GGC M.tb     GCG CAA CTG GTC GGC ACC GCC GAC CAG GTG TGG GCC GAC GCT GAT TTA TTG CTC
M.bovis  GCG CAA CTG GTC GGC ACC GCC GAC CAG GTG TGG GCC GAC GCT GAT TTA TTG CTC M.tb     AAG GTC AAA GAA CCG ATA GCG GCG GAA TAC GGC CGC CTG CGA CAC GGG CAG ATC
M.bovis  AAG GTC AAA GAA CCG ATA GCG GCG GAA TAC GGC CGC CTG CGA CAC GGG C*GA TCT M.tb     TTG TTC ACG TTC TTG CAT TTG GCC GCG TCA CGT GCT TGC ACC GAT GCG T*G TTG
M.bovis  TGT TCA CGT TCT TGC ATT TGG CCG CGT CAC GTG CTT GCA CCG ATG CGT TGT TGG M.tb     GAT TCC GGC ACC ACG TCA ATT GCC TAC GAG ACC GTC CAG ACC GCC GAC GGC GCA
M.bovis  ATT CCG GCA CCA CGT CAA TTG CCT ACG AGA CCG TCC AGA CCG CCG ACG GCG CAC M.tb     CTA CCC CTG CTT GCC CCG ATG AGC GAA GTC GCC GGT CGA CTC GCC GCC CAG GTT
M.bovis  TAC CCC TGC TTG CCC CGA TGA M.tb     GGC GCT TAC CAC CTG ATG CGA ACC CAA GGG GGC CGC GGT GTG CTG ATG GGC GGG M.tb     GTG CCC GGC GTC GAA CCG GCC GAC GTC GTG GTG ATC GGC GCC GGC ACC GCC GGC M.tb     TAC AAC GCA GCC CGC ATC GCC AAC GGC ATG GGC GCG ACC GTT ACG GTT CTA GAC M.tb     ATC AAC ATC GAC AAA CTT CGG CAA CTC GAC GCC GAG TTC TGC GGC CGG ATC CAC M.tb     ACT CGC TAC TCA TCG GCC TAC GAG CTC GAG GGT GCC GTC AAA CGT GCC GAC CTG M.tb     GTG ATT GGG GCC GTC CTG GTG CCA GGC GCC AAG GCA CCC AAA TTA GTC TCG AAT M.tb     TCA CTT GTC GCG CAT ATG AAA CCA GGT GCG GTA CTG GTG GAT ATA GCC ATC GAC M.tb     CAG GGC GGC TGT TTC GAA GGC TCA CGA CCG ACC ACC TAC GAC CAC CCG ACG TTC M.tb     GCC GTG CAC GAC ACG CTG TTT TAC TGC GTG GCG AAC ATG CCC GCC TCG GTG CCG M.tb     AAG ACG TCG ACC TAC GCG CTG ACC AAC GCG ACG ATG CCG TAT GTG CTC GAG CTT M.tb     GCC GAC CAT GGC TGG CGG GCG GCG TGC CGG TCG AAT CCG GCA CTA GCC AAA GGT M.tb     CTT TCG ACG CAC GAA GGG GCG TTA CTG TCC GAA CGG GTG GCC ACC GAC CTG GGG M.tb     GTG CCG TTC ACC GAG CCC GCC AGC GTG CTG GCC TGA
```

B

```
M.tb     MRVGIPTETKNNEFRVAITPAGVAELTRRGHEVLIQAGAGEGSAITDADFKAAGAQLVGTADQVWADADLL
M.bovis  MRVGIPTETKNNEFRVAITPAGVAELTRRGHEVLIQAGAGEGSAITDADFKAAGAQLVGTADQVWADADLL M.tb     LKVKEPIAAEYGRLRHGQILFTFLHLAASRACTDALLDSGTTSIAYETVQTADQALPLLAPMSEVAGRLAA
M.bovis  LKVKEPIAAEYGRLRHGSCSRSCINPREVLAFMRCNIPAFRQLPTRPSRPPTAHYPCLPR- M.tb     QVGAYHLMRTQGGRGVLMGGVPGVEPADVVVIGAGTAGYNAARIANGMGATVTVLDINIDKLRQLDAHFCG M.tb     RIHTRYSSAYELEGAVKRADLVIGAVLVPGAKAPKLVSNSLVAHMKPGAVLVDIAIDQGGCFEGSRPTTYD M.tb     HPTPAVHDTLFYCVANMPASVPKTSTYALTNATMFYVLELADHGWRAACRSNPALAKGLSTHEGALLSERV M.tb     ATDLGVPFTEPASVLA-
```

Fig. 9

TUBERCULOSIS VACCINES INCLUDING RECOMBINANT BCG STRAINS EXPRESSING ALANINE DEHYDROGENASE, SERINE DEHYDRATASE AND/OR GLUTAMINE SYNTHETASE

CROSS-REFERENCE TO RELATED APPLICATIONS

This application claims the benefit of U.S. Provisional Application No. 60/372,450, filed on Apr. 16, 2002.

FIELD OF THE INVENTION

This invention relates to tuberculosis (TB) vaccines.

BACKGROUND OF THE INVENTION

TB is a deadly contagious disease caused by the infectious agent, *Mycobacteriu tuberculosis*. It kills 2 million people each year. The World Health Organization (WHO) 2001 annual report estimated that there would be 8.4 million new TB cases in 1999, up from 8.0 million in 1997. If the present trend continues, it is estimated that between 2000 and 2020, nearly one billion people will be newly infected, 200 million people will become ill and 35 million will die from TB. The spread of HIV/AIDS and the emergence of multidrug-resistant TB contribute to the worsening impact of this disease. Bacille Calmette-Guerin (BCG), an attenuated strain of *Mycobacterium bovis*, is currently the only available vaccine for the prevention of TB. In animal models of infection, BCG vaccination has been demonstrated to induce protective immunity against a M tuberculosis challenge (Baldwin et al., 1998). In humans, BCG vaccination has demonstrated consistent protection against the childhood forms of TB, especially meningitis. However, BCG vaccination is controversial due to variations in its efficacy for protecting adults from pulmonary TB (Fine, 1989; Colditz et al. , 1994; Sterne et al., 1998). Trials conducted in the 1940s and 1950s in developed countries such as the United Kingdom, Denmark and North America demonstrated the vaccine to be highly efficient (70-80%). However, in the single largest clinical trial, which took place in India in 1970s and involved more than 265,000 persons, BCG vaccination provided no detectable protection against pulmonary TB. Thus, there is an urgent need to generate an improved vaccine(s) to replace the BCG and to prevent TB.

Several explanations have been suggested for the variation in protective efficacy of BCG (Andersen, 2001). The most prominent hypothesis is that exposure to environmental mycobacteria sensitizes the host against mycobacteria in general, thereby providing heterologus immunity that obscures the potential benefits of BCG vaccination (Fine, 1995; Fine and Vynnycky, 1998). Furthermore, a recent study showed that the multiplication of BCG was inhibited in animals sensitized with environmental mycobacteria, and consequently BCG vaccination elicited only a transient immune response and failed to provide protective immunity against TB (Brandt et al., 2002). This study also supports the long-standing observation that the induction of immunity to TB requires productive infection by BCG. BCG is a live vaccine; killed BCG does not provide protection. Like *M. tuberculosis*, BCG is capable of forming granulomas and abscesses in various tissues in the infected host (Hogan et al., 2001). The ability of *M. tuberculosis* and *M. bovis* BCG to survive and persist within granulomas, a hostile environment with restricted access to nutrients and reduced oxygen tension, appears to be dependent on the ability of the bacteria to adapt their metabolism to the available source of carbohydrate, nitrogen, and energy (Barclay and Wheeler, 1989). A recent study revealed that fatty acids serve as a source of carbohydrates and are required for persistence of *M. tuberculosis* in mice and activated macrophages (McKinney et al., 2000). Following vaccination in immunocompetent individuals, BCG may persist for certain periods before it is eliminated from the host (Dunn and North 1995; Lagranderie et al., 1996; Moisan et al., 2001).

The key to developing a new and effective TB vaccine is to provide long-term protection (Orme, 2001; Young, 2000). Existing BCG vaccines impart protection against the manifestations of TB in children, but their efficacy wanes over a period of 10 to 15 years, presumably because the protective immunity induced by BCG is gradually lost (Orme, 2001). New strategies to developing an improved vaccine have included the use of attenuated mycobacteria, subunit vaccines and DNA vaccines (Andersen, 2001). However, none of these have proved to be more potent than, or even as effective as BCG. Survival and growth of *M. bovis* BCG is necessary for eliciting protective immunity. It has been shown that early treatment of infected mice with isoniazid to inhibit bacillary growth prevents the development of acquired resistance. BCG strains that persist for extended periods within the host are required in order to obtain more effective vaccines. As such, there is a need for novel, recombinant strains of Bacille Calmette-Guérin.

SUMMARY OF THE INVENTION

The invention provides vaccines that overcome the limited ability of BCG strains to use naturally occurring amino acids as the nitrogen source for growth. Furthermore, L-alanine, D-alanine, or L-serine inhibits the growth of BCG strains even when ammonium is present. Expressing a functional alanine dehydrogenase [SEQ ID NO:1; SEQ ID NO: 2] in BCG strains relieves the growth inhibition of BCG by alanine. Similarly, expressing a functional L-serine dehydratase [SEQ ID NO:5; SEQ ID NO: 6] in BCG strains relieves the growth inhibition of BCG by L-serine. The mechanism for such inhibition occurs through blockage of glutamine synthetase. Overexpression of glutamine synthetase [SEQ ID NO:7] to [SEQ ID NO: 14] in BCG relieves the growth inhibition of BCG by alanine and L-serine. Recombinant BCG strains that express (or overexpress) a functional alanine dehydrogenase [SEQ ID NO:1; SEQ ID NO: 2], a L-serine dehydratase [SEQ ID NO:5; SEQ ID NO: 6], and/or glutamine synthetase [SEQ ID NO:7] to [SEQ ID NO: 14] survive and persist longer within the host and consequently induce long-term protective immunity. Such persistent recombinant BCG strains provide more effective vaccines for the prevention of TB and other mycobacterial infections.

The present invention relates to recombinant *Mycobacterium bovis* BCG, which express DNA encoding an alanine dehydrogenase [SEQ ID NO:1; SEQ ID NO: 2], a L-serine dehydratase [SEQ ID NO:5; SEQ ID NO: 6], and/or a glutamine synthetase [SEQ ID NO:7] to [SEQ ID NO: 14]. We found that, due to the lack of a functional alanine dehydrogenase [SEQ ID NO:3; SEQ ID NO: 4], BCG cannot utilize alanine (L-alanine or D-alanine) as the only nitrogen source for growth. We further found that alanine (L-alanine or D-alanine) inhibits the growth of all BCG vaccine strains. Said inhibition is relieved by expressing a functional alanine dehydrogenase [SEQ ID NO:1; SEQ ID NO: 2] in BCG. Similarly, BCG cannot utilize L-serine as the only nitrogen source for growth and that growth of BCG is inhibited by L-serine.

Expressing a L-serine dehydratase [SEQ ID NO:5; SEQ ID NO: 6] in BCG strains relieves the growth inhibition by L-serine.

Alanine (L-alanine or D-alanine) and L-serine inhibits BCG growth likely by blocking the activity of glutamine synthetase [SEQ ID NO:7] to [SEQ ID NO: 14]. Overexpression of glutamine synthetase [SEQ ID NO:7] to [SEQ ID NO: 14] in BCG relieves the growth inhibition of BCG by alanine and L-serine. Glutamine synthetase, in conjunction with glutamate synthase, provides glutamine and glutamate, which are essential for biosynthesis of all amino acids, proteins, purines and pyrmidines. Inhibition of glutamine synthetase stops cell growth. Supplying amino acids that can be converted to glutamate such as L-glutamine, L-glutamate, L-aspartate, and L-asparagine can relieve such inhibition. Indeed, our data show that the inhibition of BCG growth by alanine (L-alanine or D-alanine) or L-serine is relieved by supplementing growth medium with L-glutamine, L-glutamate, L-aspartate, or L-asparagine.

Since BCG is a live vaccine, recombinant BCG strains expressing or overexpressing a functional alanine dehydrogenase [SEQ ID NO:1; SEQ ID NO: 2], a L-serine dehydratase [SEQ ID NO:5; SEQ ID NO: 6], and/or a glutamine synthetase [SEQ ID NO:7] to [SEQ ID NO: 14] survive longer within the human host and subsequently induce long-term memory immunity. These recombinant BCG strains provide extremely useful vaccines.

The present invention relates to a live recombinant *Mycobacterium bovis*-BCG strain comprising a nucleic acid capable of expression, the nucleic acid encoding at least one protein or polypeptide that exhibits alanine dehydrogenase activity [SEQ ID NO: 1; SEQ ID NO:2], glutamine synthetase activity [SEQ ID NO:7 to SEQ ID NO:14], or L-serine dehydratase activity [SEQ ID NO:5; SEQ ID NO:6].

The invention also relates to a live recombinant *Mycobacterium bovis*-BCG strain comprising a nucleic acid capable of expression, the nucleic acid encoding at least one protein or polypeptide selected from the group consisting of alanine dehydrogenase [SEQ ID NO:1; SEQ ID NO:2], glutamine synthetase [SEQ ID NO:7 to SEQ ID NO:14] and L-serine dehydratase [SEQ ID NO:5; SEQ ID NO:6].

The invention further relates to a live recombinant *Mycobacterium bovis*-BCG strain comprising a nucleic acid capable of expression, the nucleic acid comprises all or part of at least one nucleic acid molecule selected from the group consisting of [SEQ ID NO:1], [SEQ ID NO:2], [SEQ ID NO:5], [SEQ ID NO:6], [SEQ ID NO:7], [SEQ ID NO:8], [SEQ ID NO:9], [SEQ ID NO: 10], [SEQ ID NO: 11], [SEQ ID NO: 12], [SEQ ID NO: 13] and [SEQ ID NO:14].

In one embodiment, the live recombinant *Mycobacterium bovis*-BCG strain is selected from the group consisting of *Mycobacterium bovis*-BCG-Russia, *Mycobacterium bovis*-BCG-Moreau, *Mycobacterium bovis*-BCG-Japan, *Mycobacterium bovis*-BCG-Sweden, *Mycobacterium bovis*-BCG-Birkhaug, *Mycobacterium bovis*-BCG-Prague, *Mycobacterium bovis*-BCG-Glaxo, *Mycobacterium bovis*-BCG-Denmark, *Mycobacterium bovis*-BCG-Tice, *Mycobacterium bovis*-BCG-Frappier, *Mycobacterium bovis*-BCG-Connaught, *Mycobacterium bovis*-BCG-Phipps, and *Mycobacterium bovis*-BCG-Pasteur.

Another aspect of the invention is a pharmaceutical composition comprising a live recombinant *Mycobacterium bovis*-BCG strain comprising a nucleic acid capable of expression, the nucleic acid encoding at least one protein or polypeptide that exhibits alanine dehydrogenase activity [SEQ ID NO:1; SEQ ID NO:2], glutamine synthetase activity [SEQ ID NO:7 to SEQ ID NO:14], or L-serine dehydratase activity [SEQ ID NO:5; SEQ ID NO:6].

The invention also relates to a live recombinant *Mycobacterium bovis*-BCG strain comprising a nucleic acid capable of expression, the nucleic acid encoding at least one protein or polypeptide selected from the group consisting of alanine dehydrogenase [SEQ ID NO:1; SEQ ID NO:2], glutamine synthetase [SEQ ID NO:7 to SEQ ID NO:14] and L-serine dehydratase [SEQ ID NO:5; SEQ ID NO:6].

In yet another aspect of the invention there is a pharmaceutical composition comprising a live recombinant *Mycobacterium bovis*-BCG strain comprising a nucleic acid capable of expression, the nucleic acid comprises all or part of at least one nucleic acid molecule selected from the group consisting of [SEQ ID NO:1], [SEQ ID NO:2], [SEQ ID NO:5], [SEQ ID NO:6], [SEQ ID NO:7], [SEQ ID NO:8], [SEQ ID NO:9], [SEQ ID NO:10], [SEQ ID NO: 11], [SEQ ID NO:12], [SEQ ID NO:13] and [SEQ ID NO:14].

In a further aspect of the invention there is a vaccine or immunogenic composition for treatment or prophylaxis of a mammal against challenge by mycobacteria comprising a live recombiant *Mycobacterium bovis*-BCG strain comprising a nucleic acid capable of expression, the nucleic acid encoding at least one protein or polypeptide that exhibits alanine dehydrogenase activity [SEQ ID NO:1; SEQ ID NO:2], glutamine synthetase activity [SEQ ID NO:7 to SEQ ID NO:14], or L-serine dehydratase activity [SEQ ID NO:5; SEQ ID NO:6].

In another aspect of the invention there is a vaccine or immunogenic composition for treatment or prophylaxis of a mammal against challenge by mycobacteria comprising a live recombiant *Mycobacterium bovis*-BCG strain comprising a nucleic acid capable of expression, the nucleic acid encoding at least one protein or polypeptide selected from the group consisting of alanine dehydrogenase [SEQ ID NO:1; SEQ ID NO:2], glutamine synthetase [SEQ ID NO:7 to SEQ ID NO:14] and L-serine dehydratase [SEQ ID NO:5; SEQ ID NO:6].

In yet another aspect of the invention there is a vaccine or immunogenic composition for treatment or prophylaxis of a mammal against challenge by mycobacteria comprising a live recombinant *Mycobacterium bovis*-BCG strain comprising a nucleic acid capable of expression, the nucleic acid comprises all or part of at least one nucleic acid molecule selected from the group consisting of [SEQ ID NO:1], [SEQ ID. NO:2], [SEQ ID NO:5], [SEQ ID NO:6], [SEQ ID NO:7], [SEQ ID NO:8], [SEQ ID NO:9], [SEQ ID NO:10], [SEQ ID NO:11 ],[SEQ ID NO:12],[SEQ ID NO:13] and [SEQ ID NO:14]. In a preferred embodiment the vaccine or immunogenic composition is for the treatment or prophylaxis of a mammal against challenge by *Mycobacterium tuberculosis*. In another preferred embodiment the vaccine or immunogenic compositions of the current invention further comprise a pharmaceutically acceptable carrier. In yet another preferred embodiment the vaccine or immunogenic compositions further comprise adjuvants. In a another embodiment the vaccine or immunogenic compositions further comprises immunogenic materials from one or more other pathogens.

Another aspect of this invention relates to a method for treatment or prophylaxis of a mammal against challenge by *Mycobacterium tuberculosis* or *Mycobacterium bovis* comprising administering to the mammal a vaccine or immunogenic composition of the instant invention. In one embodiment the mammal is a cow. In another embodiment the mammal is a human. In yet another embodiment the vaccine or immunogenic composition is administered in the presence of an adjuvant.

A further aspect of the invention is a method for the treatment or prophylaxis of a mammal against cancer comprising administering to the mammal a vaccine or immunogenic composition of the current invention. In one embodiment the cancer is bladder cancer. In another embodiment the vaccine or immunogenic composition is administered in the presence of an adjuvant.

The invention also relates to a test kit comprising the live recombinant *Mycobacterium bovis*-BCG strain of the instant invention.

The invention further relates to a media composition for inhibiting the growth of *Mycobacterium bovis*-BCG comprising alanine as the only nitrogen source for growth. In another embodiment serine is the only nitrogen source for growth. In another embodiment, the media compositions of the current invention further comprise a carbon source, iron, magnesium, and $SO_4$. In one embodiment the carbon source is selected from the group consisting of glycerol, dextrose, citrate, and glucose.

The current invention relates to a method for inhibiting the growth of *Mycobacterium bovis*-BCG comprising the steps of (a) obtaining a sample comprising *Mycobacterium* and (b) culturing the sample in a selective media. In one embodiment the selective media comprises alanine as the only nitrogen source. In yet another embodiment the selective media comprises serine as the only nitrogen source.

Another aspect of the invention relates to a method for culturing *Mycobacterium bovis*-BCG comprising the steps of (a) obtaining a sample comprising *Mycobacterium* and (b) culturing the sample in differential media. In one embodiment the differential media comprises histidine.

BRIEF DESCRIPTION OF THE DRAWINGS

Preferred embodiments of the invention will be described in relation to the drawings in which.

Cloning of sdaA [SEQ ID NO:5] was accomplished in two steps. First, a 9.5 kb BamHI fragment of *M. tuberculosis* genomic DNA was ligated to BamHI-linearized pMD31 to generate pSDA1. Plasmid pSDAA was generated by cleavage of pSDA1 with PstI, followed by self-ligation of the 10.9 kb PstI fragment.

Figure 1:
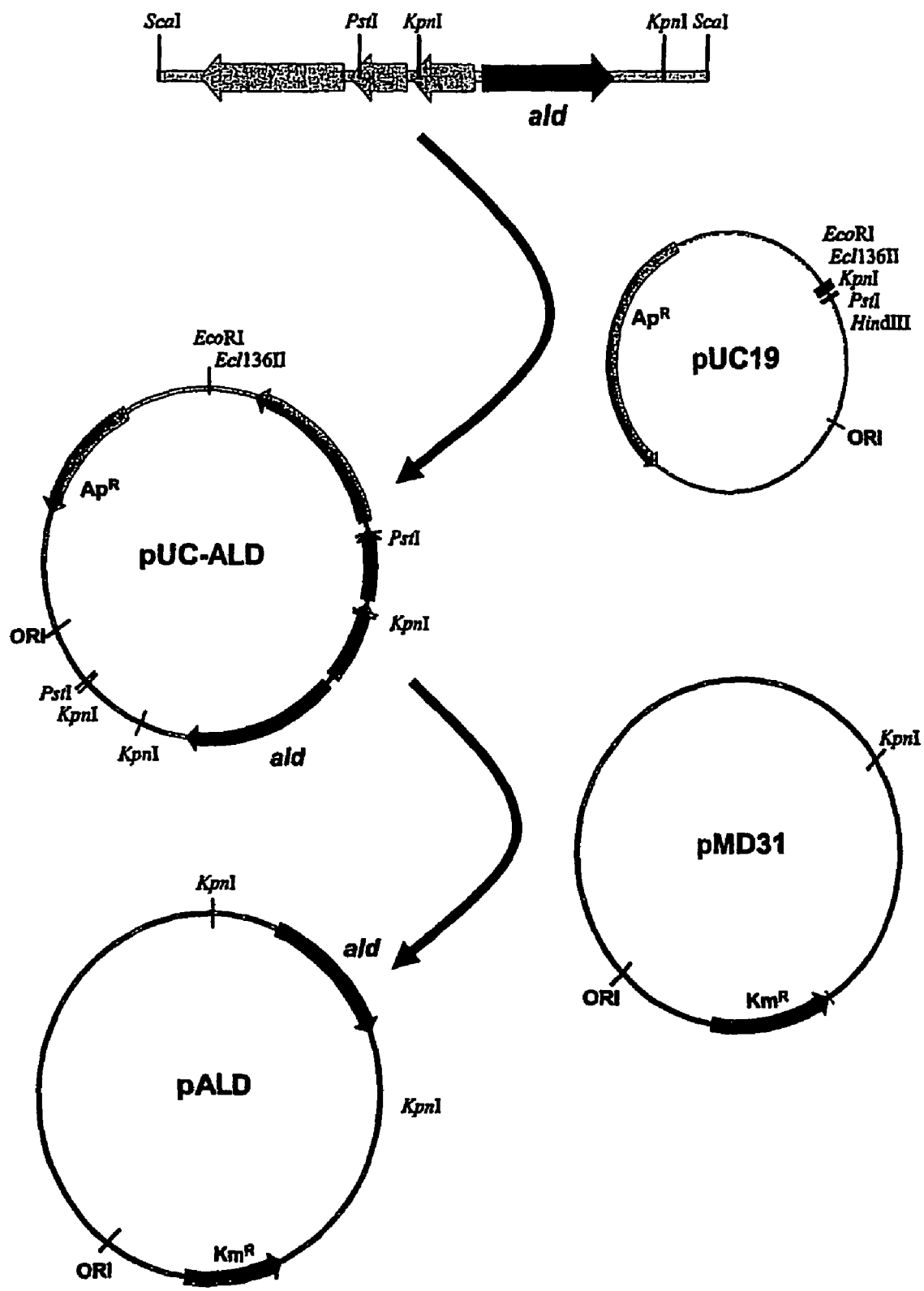
FIG. 1. Cloning of the ald gene. First, a 4.5 kb ScaI fragment of *M. tuberculosis* genomic DNA containing the ald gene [SEQ ID NO:1] was ligated to Ecl136II-linearized pUC19 to generate pUC-ALD. Then, mycobacterial plasmid pALD was created by ligating the 1.9 kb KpnI fragment containing the ald gene [SEQ ID NO:1] to KpnI-linearized pMD31.
Figure 2:
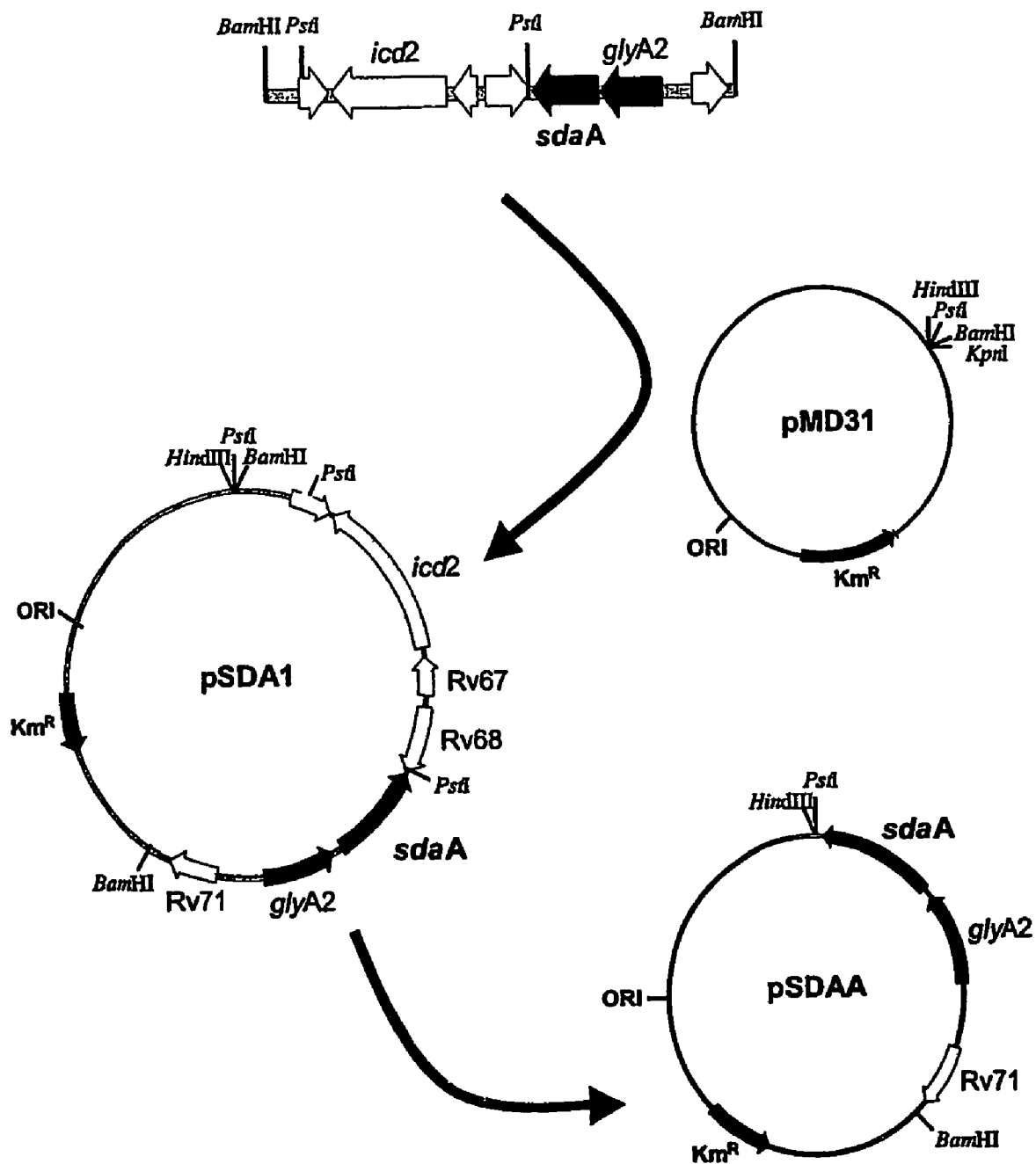
FIG. 2. Cloning of the sdaA gene.
Figure 3:
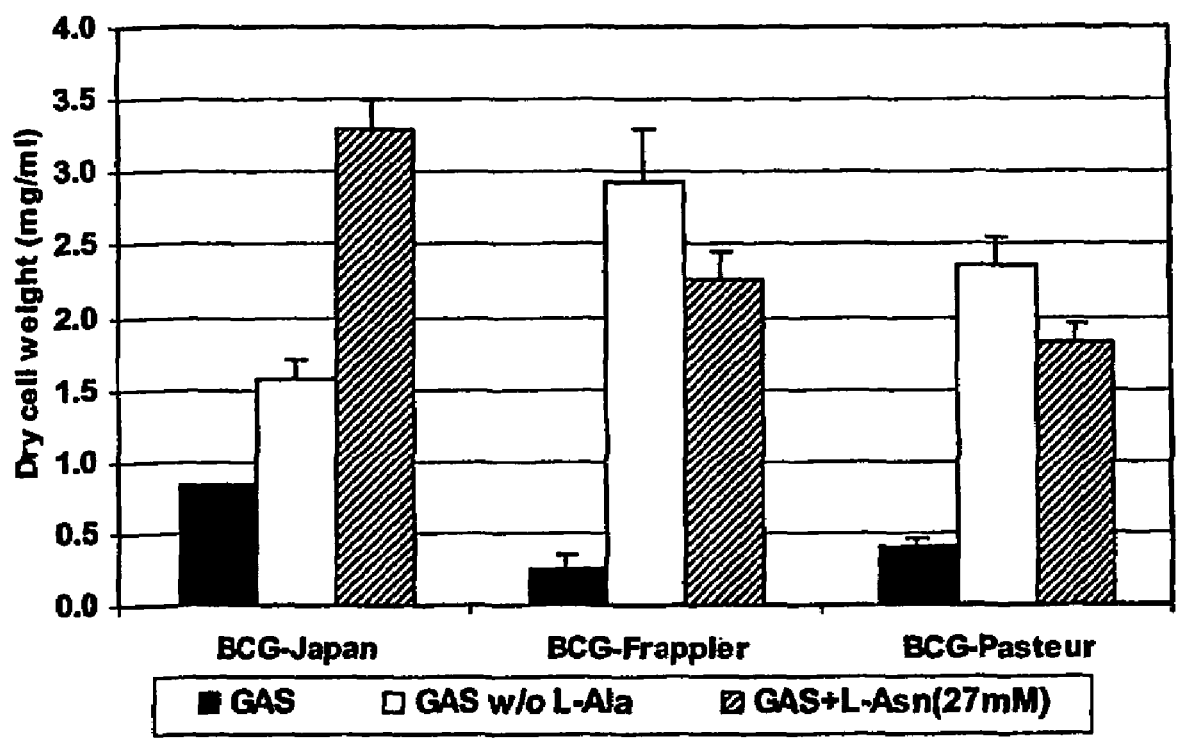

FIG. 3. Inhibition of BCG growth by L-alanine in GAS. BCG-Japan, BCG-Frappier, and BCG-Pasteur grown to stationary phase in 7H9/ADC/glycerol/Tween-80 liquid media, were each inoculated into duplicate 5 ml culture volumes of GAS, GAS without L-alanine, and GAS supplemented with 27 mM L-asparagine, to a cell density of $2\times10^7$ cells/ml. Cultures were incubated at 37° C. with constant shaking for 16 days and then 2 ml aliquots of cell culture were centrifuged and cell pellet lyophilized to determine cell dry weight.

Figure 4:
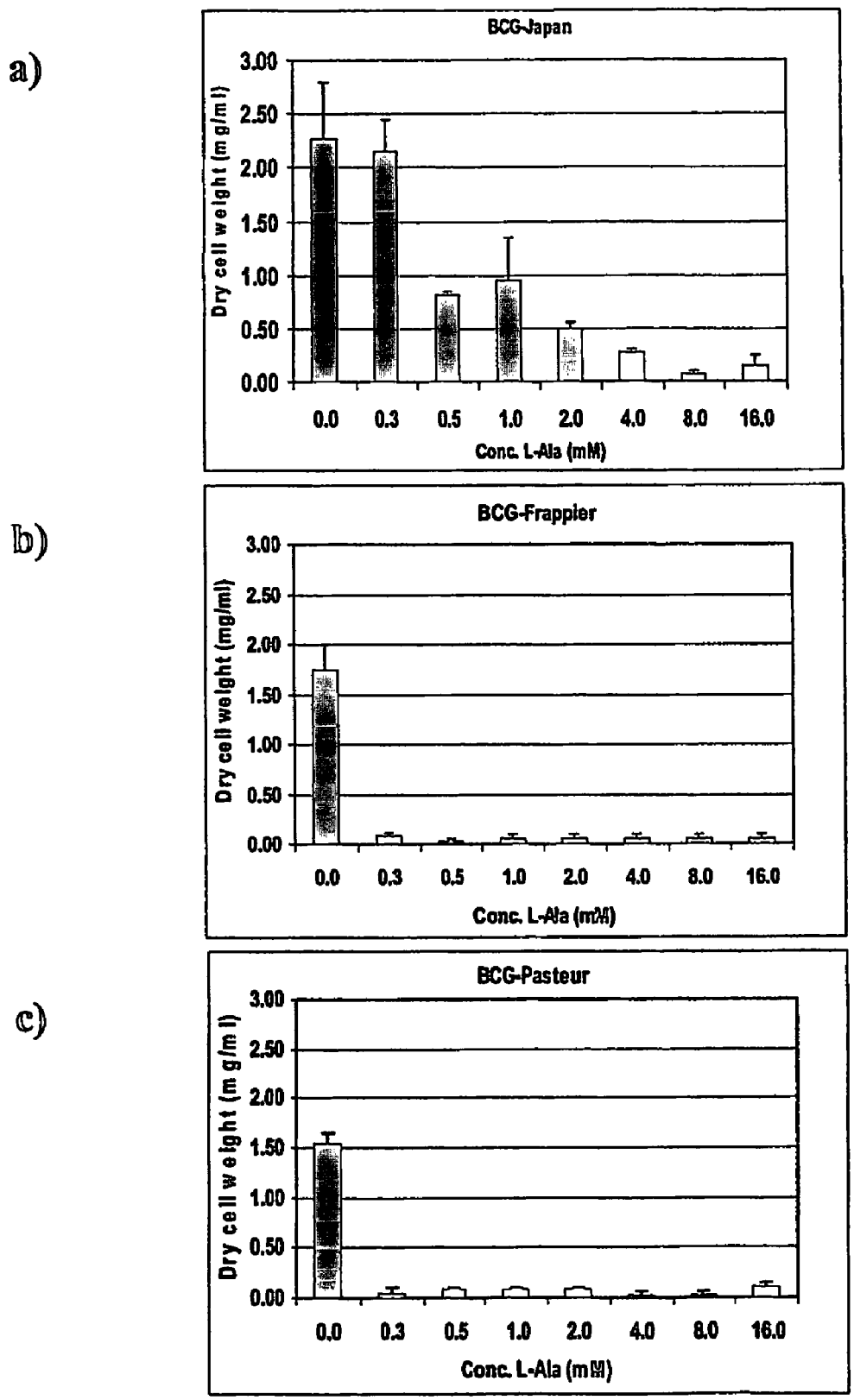

FIG. 4. Inhibition of BCG growth by increasing concentrations of L-alanine in Sauton containing $NH_4Cl$ (5 g/liter). a) BCG-Japan, b) BCG-Frappier, and c) BCG-Pasteur, grown to stationary phase in 7H9/ADC/glycerol/Tween-80 liquid media. Cells were washed and resuspended in Sauton basal medium (no nitrogen source).

Resuspended cells of each strain were inoculated into duplicate 5 ml culture volumes of Sauton media supplemented with $NH_4Cl$ and increasing concentrations of L-alanine. Cultures were incubated at 37° C. with constant shaking for 30 days and cell dry weight was determined.

Figure 5:
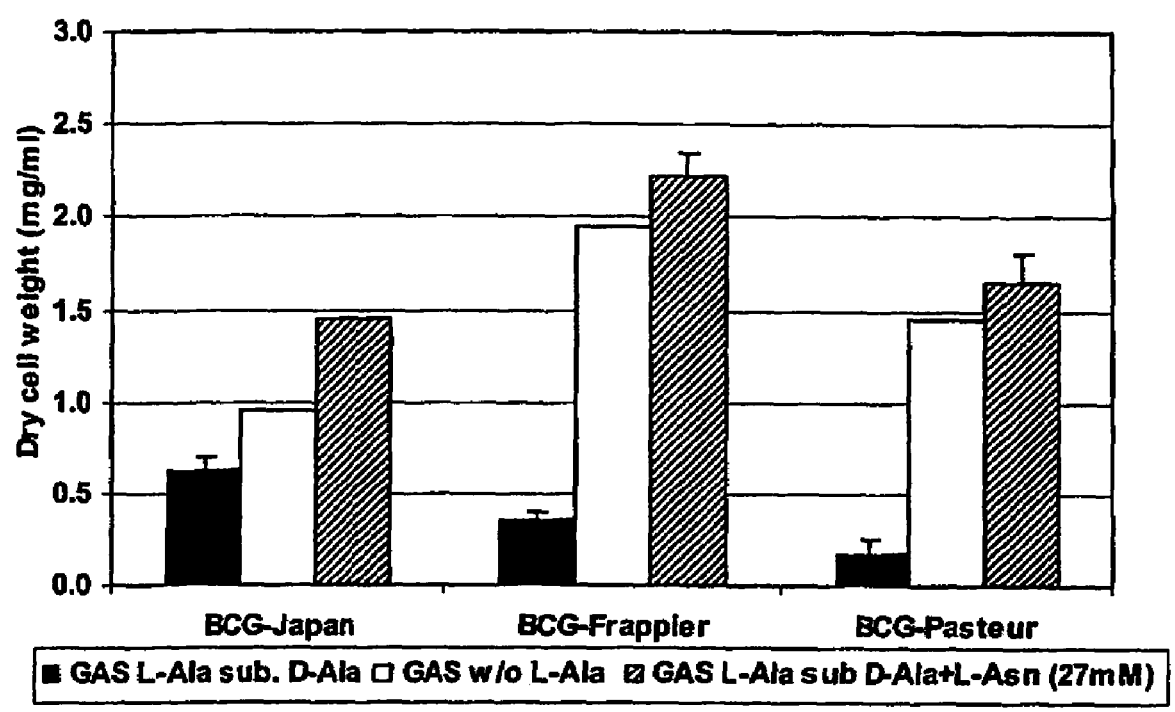

FIG. 5. Inhibition of BCG growth by D-alanine in GAS. BCG-Japan, BCG-Frappier, and BCG-Pasteur grown to stationary phase in 7H9/ADC/glycerol/Tween-80 liquid media, were each inoculated into 5 ml culture volumes of GAS in which L-alanine was replaced by D-alanine, GAS without L-alanine and, GAS (containing D-alanine) supplemented with 27 mM L-asparagine, to a cell density of $2\times10^7$ cells/ml. Cultures were incubated at 37° C. with constant shaking for 13 days and cell dry weight was determined.

Figure 6:
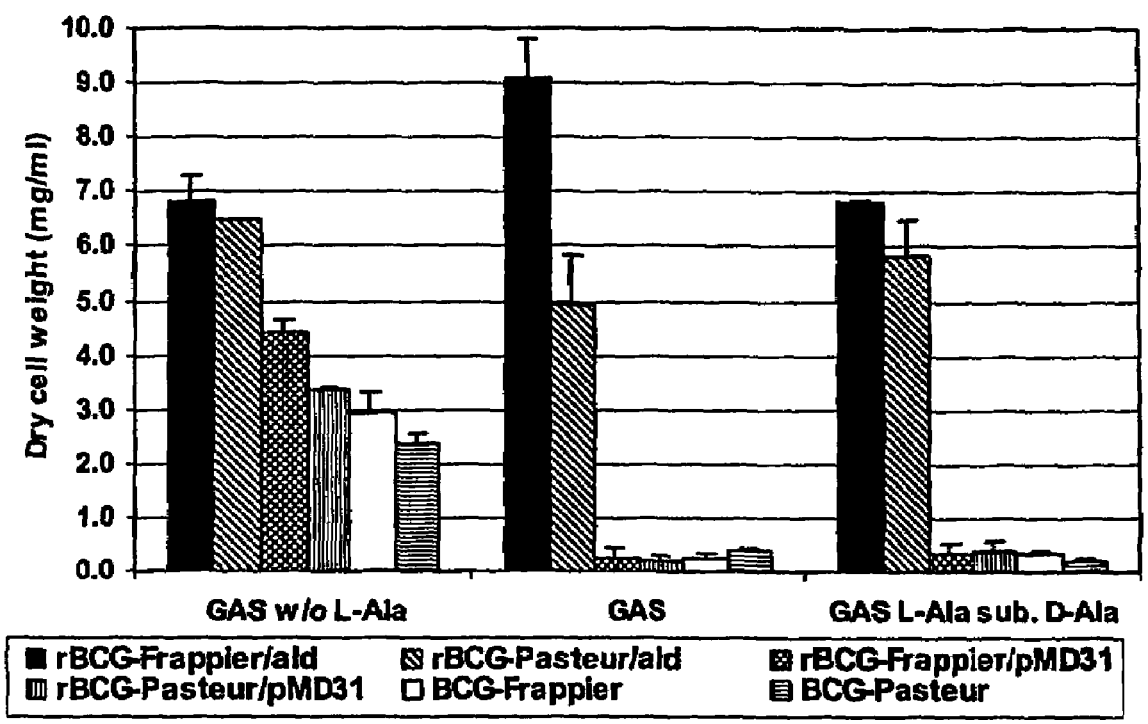

FIG. 6. Growth of recombinant BCG strains expressing alanine dehydrogenase [SEQ ID NO:1] in GAS medium. The growth of BCG-Frappier/ald, BCG-Pasteur/ald, BCG-Frappier/pMD31, BCG-Pasteur/pMD31, BCG-Frappier, and BCG-Pasteur were compared. Cells of each strain, grown to stationary phase in 7H9/ADC/glycerol/Tween-80 liquid media, were washed and resuspended in Sauton basal medium (no nitrogen source). Resuspended cells were inoculated into duplicate 5 ml culture volumes of GAS without L-alanine, GAS containing L-alanine and GAS in which L-alanine was replaced by D-alanine. Cultures were incubated at 37° C. with constant shaking for 15 days and cell dry weight was then determined.

Figure 7:
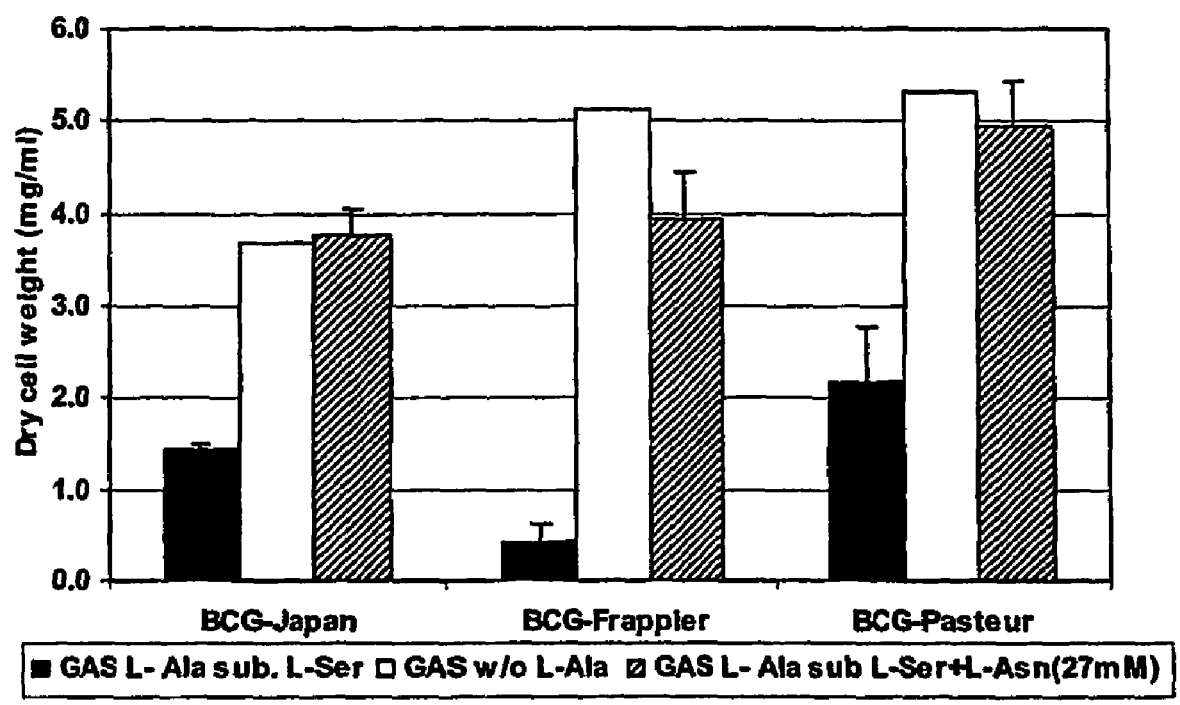

FIG. 7. Inhibition of BCG growth by L-serine in GAS. BCG-Japan, BCG-Frappier, and BCG-Pasteur grown to stationary phase in 7H9/ADC/glycerol/Tween-80 liquid media, were each inoculated into duplicate 5 ml culture volumes of GAS in which L-alanine was replaced by L-serine, GAS without L-alanine, and GAS (containing L-serine) supplemented with 27 mM L-asparagine, to a cell density of $2\times10^7$ cells/ml. Cultures were incubated at 37° C. with constant shaking for 15 days and cell dry weight was then determined.

Figure 8:
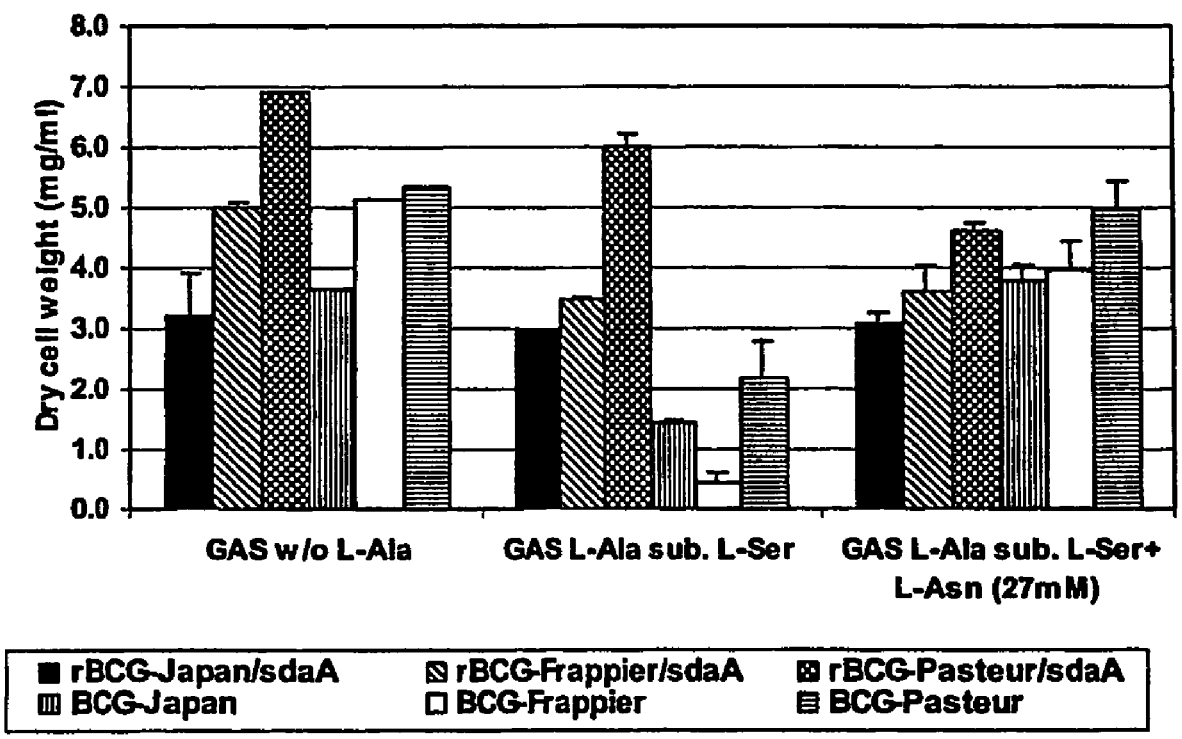

FIG. 8. Growth of recombinant BCG strains expressing L-serine dehydratase [SEQ ID NO:5] in GAS medium containing L-serine. The growth of BCG-Japan/sdaA, BCG-Frappier/sdaA, BCG-Pasteur/sdaA, BCG-Japan, BCG-Frappier, and BCG-Pasteur were compared. Cells of each strain, grown to stationary phase in 7H9/ADC/glycerol/Tween-80 liquid media, were washed and resuspended in Sauton basal medium (no nitrogen source). Resuspended cells were inoculated into duplicate 5 ml culture volumes of GAS without L-alanine, GAS in which L-alanine was replaced by L-serine, and GAS (containing L-serine) supplemented with 27 mM L-asparagine. Cultures were incubated at 37° C. with constant shaking for 15 days and cell dry weight was then determined.

FIG. 9. Alignment of A) nucleotide and B) amino acid sequences of the ald genes of *Mycobacterium tuberculosis* (*M. tb*) [SEQ ID NO:1; SEQ ID NO:2] and *Mycobacterium bovis* (*M. bovis*) [SEQ ID NO:3; SEQ ID NO:4]. The point deletion causing the frameshift mutation in *M. bovis* ald [SEQ ID NO:3] is indicated with an arrow. Nucleotide codons and amino acids affected by this mutation are highlighted.

DETAILED DESCRIPTION OF THE INVENTION

BCG vaccine strains have a limited ability to utilize amino acids as the nitrogen source for growth. Furthermore, we found that naturally occurring amino acids L-alanine and L-serine inhibit the growth of BCG strains. Expressing a functional L-alanine dehydrogenase [SEQ ID NO:1; SEQ ID NO:2] in BCG relieves the growth inhibition by alanine. Expressing of a functional L-serine dehydratase [SEQ ID NO:5; SEQ ID NO:6] in BCG relives the growth inhibition by L-serine. As well, overproduction of glutamine synthetase [SEQ ID NO:7] to [SEQ ID NO: 14] relieves the growth inhibition by alanine and serine. These novel findings are significant because recombinant BCG strains that express (or overexpress) a functional alanine dehydrogenase [SEQ ID NO:1; SEQ ID NO:2], a L-serine dehydratase [SEQ ID NO:5; SEQ ID NO:6], and/or glutamine synthetase [SEQ ID NO:7] to [SEQ ID NO: 14] will survive better within the human host, induce long-term memory immunity and provide for more effective vaccines to prevent TB, particularly for protecting against pulmonary TB in adults.

It has long been known that administration of killed BCG strains results in a weak and transient immune response. Protective immunity requires survival and replication of BCG in the vaccinated host. This notion is reinforced by a recent study of an animal model of infection, which showed that prior exposure to live environmental mycobacteria blocked the multiplication of BCG in infected mice. Consequently BCG elicited only a transient immune response which failed to provide protective immunity against TB (Brandt et al., 2002). Live BCG continuously secrete many different antigens that are likely important for the induction of protective immunity. The continuous production of numerous antigens by multiplying BCG gives live vaccines an advantage over subunit vaccines or DNA vaccines which transiently produce a few antigens. Thus the ability of BCG to multiply and persist within the host is an important determinant of BCG efficacy.

In order to grow and persist within the host, BCG must be able to utilize the available nutrients inside the host. It was demonstrated that isocitrate lyase, an essential enzyme for catabolism of fatty acids, is required for persistence of *M. tuberculosis* during the chronic phase of infection and that this requirement was dependent on an intact immune response of the host (McKinney et al., 2000). In another study, an *M. bovis* BCG strain lacking anaerobic nitrate reductase, an enzyme essential for nitrate respiration, failed to persist in lungs, liver and kidneys of immune-competent mice (Fritz et al., 2002). Our findings, that BCG strains utilize only a few types of amino acids as the nitrogen source for growth, and that the growth of all BCG strains are inhibited by naturally occurring L-alanine and L-serine, suggest that the ability of BCG to grow and persist within the host is restricted. The concentration of L-alanine that is available to BCG growing in human is estimated to be 0.33-0.42 mM (Barclay and Wheeler, 1989), which is sufficient to inhibit the growth of BCG-Pasteur or BCG-Frappier, and significantly reduce the growth of BCG-Japan (FIG. 4). The concentration of L-serine present in the extracellular fluids of the host is around 0.1 mM (Barclay and Wheeler, 1989), which may cause significant inhibition of BCG growth. Since multiplication of BCG is required to generate protective immunity, such inhibition by amino acids within the host may prevent the development of long-term protective immunity and hence the lack of protection against pulmonary TB in adults.

*M. bovis* BCG is also used in the treatment of bladder cancer. Numerous randomized controlled clinical trials indicate that intravesical administration of BCG can prevent or delay tumour recurrence (reviewed in Lamm, 2000; Lockyer and Gillatt, 2001). The details of how BCG exerts this effect remain to be determined. However, the antitumour response requires an intact T-cell response, and involves increased expression of Th1-type cytokines, including TNFα and IL-6 (reviewed in Prescott et al, 2000). The most effective treatment regimes involve multiple applications of BCG, which suggests that prolonged exposure to the bacteria is required. Similarly, tumours that retain the ability to phagocytize BCG are most susceptible to this treatment (de Boer et al 1996), indicating that bacterial interactions with the tumour are important. As such, a BCG strain demonstrating increased persistence may provide enhanced antitumour activity.

We show that the absence of a functional alanine dehydrogenase [SEQ ID NO:1; SEQ ID NO:2] is responsible for the failure of BCG strains to utilize alanine (L-alanine or D-alanine) as the only nitrogen source. A gene (Rv2708) coding for a L-alanine dehydrogenase (ald) [SEQ ID NO: 1] was identified in the genome of *M. tuberculosis*. The activity of this enzyme from *M. tuberculosis* had been demonstrated biochemically in vitro. Ald converts L-alanine to pyruvate and ammonium, and is highly specific for L-alanine (Hutter and Singh, 1999). This enzyme was detected in the culture supernatent fraction of *M. tuberculosis* but not in *M. bovis* BCG-Japan nor BCG-Copenhagen, even though DNA Southern blot showed that the gene is present in both BCG strains (Anderson et al., 1992). Similarly, we do not detect alanine dehydrogenase activity in any of the 12 BCG strains listed in this report (data not shown). This lack of a functional alanine dehydrogenase in BCG strains is probably caused by a mutation within the ald gene [SEQ ID NO:3], and probably originated with the original *M. bovis* strain. A frame-shift mutation is found within the ald gene in the published genome sequence of *M. bovis* (FIG. 9) [SEQ ID NO:3]. As a result, the full length L-alanine dehydrogenase protein [SEQ ID NO:2; SEQ ID NO:4] cannot be made in BCG strains and subsequently BCG cannot catabolize alanine. Similarly, the failure of BCG to utilize L-serine as the only nitrogen source is likely to be caused by either mutations or altered expression of the sdaA gene [SEQ ID NO:5; SEQ ID NO:6], which encodes L-serine dehydratase. Expression of sdaA [SEQ ID NO:5; SEQ ID NO:6] of *M. tuberculosis* in BCG allows BCG strains to grow on L-serine as the only nitrogen source and relieves the inhibition of BCG growth by L-serine (FIG. 8). The inhibition of BCG growth by alanine and serine is caused by inhibition of glutamine synthetase [SEQ ID NO:7] to [SEQ ID NO: 14]. Overexpression of a glutamine synthetase [SEQ ID NO:7] to [SEQ ID NO: 14] in BCG relieves the growth inhibition by L-serine, L-alanine and D-alanine.

BCG-Frappier and BCG-Pasteur are more susceptible than BCG-Japan to inhibition by alanine, presumably due to difference in the expression level or activity of glutamine synthetase. BCG-Japan differs from BCG-Frappier or BCG-Pasteur genetically (Behr et al., 1999). Calmette and Guérin developed the BCG vaccine in 1921 after 13 years and 230 passages of an isolate of *M. bovis* in vitro. Starting from 1924, BCG lots were distributed to laboratories around the world. These laboratories continued the passage of the bacteria in vitro employing a variety of different recipes and protocols until 1961 when lyophilized seeds were established. As a consequence of such practices, different BCG progeny strains were created, which differed biochemically and genetically (Oettinger et al., 1999; Behr et al., 1999). Our data show that the ability of BCG strains to utilize amino acids as nitrogen source vary; for example, BCG-Japan is able to grow on cationic amino acids including L-arginine and L-lysine while BCG-Pasteur and BCG-Frappier cannot. These differences may also contribute to the differences of BCG efficacy in various clinical trials.

In summary, we use recombinant BCG strains that express (or overexpress) a functional alanine dehydrogenase [SEQ ID NO:1; SEQ ID NO:2], a L-serine dehydratase [SEQ ID NO:5; SEQ ID NO:6], and/or glutamine synthetase [SEQ ID NO:7] to [SEQ ID NO: 14] as vaccines to prevent TB and other mycobacterial infections. These recombinant BCG vaccines will induce long-term protective immunity against TB.

Variations of Nucleic Acid Molecules

Modifications

Many modifications may be made to the nucleic acid molecule DNA sequences disclosed in this application and these will be apparent to one skilled in the art. The invention includes nucleotide modifications of the sequences disclosed in this application (or fragments thereof) that are capable of directing expression in bacterial or mammalian cells. Modifications include substitution, insertion or deletion of nucleotides or altering the relative positions or order of nucleotides.

Nucleic acid molecules may encode conservative amino acid changes in alanine dehydrogenase, glutamine synthetase or L-serine dehydratase. The invention includes functionally equivalent nucleic acid molecules that encode conservative amino acid changes within alanine dehydrogenase, glutamine synthetase or L-serine dehydratase and produce silent amino acid changes in alanine dehydrogenase, glutamine synthetase or L-serine dehydratase. Methods for identifying empirically conserved amino acid substitution groups are well known in the art (see for example, Wu, Thomas D. "Discovering Emperically Conserved Amino Acid Substitution Groups in Databases of Protein Families".

Nucleic acid molecules may encode non-conservative amino acid substitutions, additions or deletions in alanine dehydrogenase, glutamine synthetase or L-serine dehydratase. The invention includes functionally equivalent nucleic acid molecules that make non-conservative amino acid changes within the amino acid sequences in [SEQ ID NO:2, 6, 8, 10, 12, or 14]. Functionally equivalent nucleic acid molecules include DNA and RNA that encode peptides, peptides and proteins having non-conservative amino acid substitutions (preferably substitution of a chemically similar amino acid), additions, or deletions but which also retain the same or similar alanine dehydrogenase, glutamine synthetase or L-serine dehydratase activity as the alanine dehydrogenase shown in [SEQ ID NO:2], glutamine synthetase shown in [SEQ ID NO:8, 10, 12, or 14] or L-serine dehydratase shown in [SEQ ID NO:6].

The DNA or RNA can encode fragments or variants of alanine dehydrogenase, glutamine synthetase or L-serine dehydratase.

Fragments are useful as immunogens and in immunogenic compositions.

The alanine dehydrogenase, glutamine synthetase or L-serine dehydratase like-activity of such fragments and variants is identified by assays as described below.

Sequence Identity

The nucleic acid molecules of the invention also include nucleic acid molecules (or a fragment thereof) having at least about: 60% identity, at least 70% identity, at least 80% identity, at least 90% identity, at least 95% identity, at least 96% identity, at least 97% identity, at least 98% identity or, most preferred, at least 99% or 99.5% identity to a nucleic acid molecule of the invention and which are capable of expression of nucleic acid molecules in bacterial or mammalian cells. Identity refers to the similarity of two nucleotide sequences that are aligned so that the highest order match is obtained. Identity is calculated according to methods known in the art. For example, if a nucleotide sequence (called "Sequence A") has 90% identity to a portion of [SEQ ID NO: 1], then Sequence A will be identical to the referenced portion of [SEQ ID NO: 1] except that Sequence A may include up to 10 point mutations (such as substitutions with other nucleotides) per each 100 nucleotides of the referenced portion of [SEQ ID NO: 1].

Sequence identity (each construct preferably without a coding nucleic acid molecule insert) is preferably set at least about: 70% identity, at least 80% identity, at least 90% identity, at least 95% identity, at least 96% identity, at least 97% identity, at least 98% identity or, most preferred, at least 99% or 99.5% identity to the sequences provided in SEQ ID NO: 1 to SEQ ID NO: 14 or its complementary sequence). Sequence identity will preferably be calculated with the GCG program from Bioinformatics (University of Wisconsin). Other programs are also available to calculate sequence identity, such as the Clustal W program (preferably using default parameters; Thompson, J D et al., Nucleic Acid Res. 22: 4673-4680), BLAST P, BLAST X algorithms, *Mycobacterium avium* BLASTN at The Institute for Genomic Research, *Mycobacterium bovis, M. Bovis* BCG (Pastuer), *M. marinum, M. leprae, M. tuberculosis* BLASTN at the Wellcome Trust Sanger Institute *M. tuberculosis* BLAST searches at Institute Pasteur (Tuberculist), *M. leprae* BLAST searches at Institute Pasteur (Leproma), *M. Paratuberculosis* BLASTN at Microbial Genome Project, University of Minnesota and, various BLAST searches at the National Center for Biotechnology Information—USA and various BLAST searches at GenomeNet(Bioinformatics Center-Institute for Chemical Research).

Since the genetic code is degenerate, the nucleic acid sequence in [SEQ ID NO:1] is not the only sequence which may code for a polypeptide having dehydrogenase activity; the nucleic acid sequences in [SEQ ID NO:7, 9, 11, and 13] are not the only sequences which may code for a polypeptide having glutamine synthetase activity; and the nucleic acid sequence in [SEQ ID NO:5] is not the only sequence which may code for a polypeptide having L-serine dehydratase activity. This invention includes nucleic acid molecules that have the same essential genetic information as the nucleic acid molecules described in [SEQ ID NO:1, 5, 7, 9, 11 and 13]. Nucleic acid molecules (including RNA) having one or more nucleic acid changes compared to the sequences described in this application and which result in production of the polypeptides shown in [SEQ ID NO:2, 6, 8, 10, 12 and 14] are within the scope of the invention.

Other functional equivalent forms of alanine dehydrogenase-, glutamine synthetase-, and 1-serine dehydratase-encoding nucleic acids can be isolated using conventional DNA-DNA or DNA-RNA hybridization techniques.

Hybridization

The invention includes DNA that has a sequence with sufficient identity to a nucleic acid molecule described in this application to hybridize under stringent hybridization conditions (hybridization techniques are well known in the art). The present invention also includes nucleic acid molecules that hybridize to one or more of the sequences in [SEQ ID NO:1] to [SEQ ID NO:14] or its complementary sequence. Such nucleic acid molecules preferably hybridize under high stringency conditions (see Sambrook et al. Molecular Cloning: A Laboratory Manual, Most Recent Edition, Cold Spring Harbor Laboratory Press, Cold Spring Harbor, N.Y.). High stringency washes have preferably have low salt (preferably about 0.2% SSC) and a temperature of about 50-65° C.

Vaccines

One skilled in the art knows the preparation of live recombinant vaccines. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The live immunogenic ingredients are often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants that enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80™ emulsion.

The effectiveness of an adjuvant may be determined by measuring the amount of antibodies directed against an immunogenic polypeptide containing a *Mycobacterium tuberculosis* antigenic sequence resulting from administration of the live recombinant *Mycobacterium bovis*-BCG vaccines that are also comprised of the various adjuvants. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25%-70%.

The vaccines are administered in a manner compatible with the dosage formulation, and in such amount as will be prophylactically and/or therapeutically effective.

The vaccine may be given in a single dose schedule, or preferably in a multiple dose schedule. A multiple dose schedule is one in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In addition, the live recombinant *Mycobacterium bovis*-BCG vaccine administered in conjunction with other immunoregulatory agents, for example, immune globulins. A subject of the present invention is also a multivalent vaccine formula comprising, as a mixture or to be mixed, a live recombinant *Mycobacterium bovis*-BCG vaccine as defined above with another vaccine, and in particular another recombinant live recombinant *Mycobacterium bovis*-BCG vaccine as defined above, these vaccines comprising different inserted sequences.

Pharmaceutical Compositions

The pharmaceutical compositions of this invention are used for the treatment or prophylaxis of a mammal against challenge by *Mycobacterium tuberculosis* or *Mycobacterium bovis*. The pharmaceutical compositions of this invention are also used to treat patients having degenerative diseases, disorders or abnormal physical states such as cancer.

The pharmaceutical compositions can be administered to humans or animals by methods such as tablets, aerosol administration, intratracheal instillation and intravenous injection.

Media Compositions

The media compositions of this invention for inhibiting the growth of *Mycobacterium bovis*-BCG comprise alanine or serine as the only nitrogen source. When alanine is the only nitrogen source it is present in an amount of at least 0.03 mM and when serine is the only nitrogen source it is present in an amount of at least 0.03 mM.

The media compositions may further contain carbon in an amount of about 1.35 g/L to about 1.65 g/L, preferably in an amount of at least 1.5 g/L; iron in an amount of about 0.045 g/L to about 0.055 g/L, preferably in an amount of at least 0.05 g/L; magnesium in an amount of about 0.45 g/L to about 0.55 g/L, preferably in an amount of at least 0.5 g/L; and $SO_4$ in an amount of about 0.045 g/L to about 0.055 g/L, preferably in an amount of at least 0.05 g/L.

Kits

Kits suitable for immunodiagnosis and containing the appropriate labeled reagents are constructed by packaging the appropriate materials, including the live recombinant *Mycobacterium bovis*-BCG strains of the instant invention, in suitable containers, along with the remaining reagents and materials required for the conduct of the assay, as well as a suitable set of assay instructions. Any immunological test format is contemplated, such as ELISA, Western blot, sandwich assay etc., which are well known to those skilled in the art.

Materials and Methods

Bacterial strains and culture conditions. Twelve *M. bovis* BCG strains: BCG-Japan, BCG-Russia, BCG-Moreau, BCG-Sweden, BCG-Birkhaug BCG-Frappier, BCG-Pasteur, BCG-Glaxo, BCG-Phipps, BCG-Tice, BCG-Denmark, and BCG-Prague were used in this study and were obtained from Dr. Marcel Behr (McGill University). The identities of these strains were described in detail previously (Behr et al., 1999). Middlebrook 7H9 medium (Difco)-contains (per liter) ammonium sulfate, 0.5 g; L-glutamate, 0.5 g; sodium citrate 0.1 g; pyridoxine, 1 mg; biotin, 0.5 mg; disodium phosphate 2.5 g; monopotassium phosphate, 1 g; ferric ammonium citrate 40 mg; magnesium sulfate 50 mg; calcium chloride 0.5 mg; zinc sulfate 1 mg; copper sulfate, 1 mg; and glycerol, 2 ml; with 5 g of albumin (fraction V; bovine), 2 g of dextrose, and 0.05% Tween 80 added after sterilization. Sauton medium contains (per liter) L-asparagine, 4 g; monopotassium sulfate, 0.5 g; magnesium sulfate 0.5 g; ferric ammonium citrate 50 mg; citric acid, 2 g; zinc sulfate, 1 mg; and glycerol, 60 ml; with 0.05% Tween 80 added after sterilization. Glycerol-alanine-salts (GAS) medium contains (per liter) 2 g of ammonium chloride, 1 g of L-alanine, 0.3 g of Bacto Casitone (Difco), 4 g of dibasic potassium phosphate, 2 g of citric acid, 50 mg of ferric ammonium citrate, 1.2 g of magnesium chloride hexahydrate, 0.6 g of potassium sulfate, 1.8 ml of 10 M sodium hydroxide, and 10 ml of glycerol. Tween 80 was added to 0.05% after sterilization. BCG cultures were grown at 37° C. with constant shaking for 3-4 weeks.

Cloning of ald. Cloning of ald [SEQ ID NO:1] was accomplished in two steps (FIG. 1). First, a 4.5 kb ScaI fragment of *M. tuberculosis* genomic DNA containing ald was ligated to Ecl136II-linearized pUC19. to generate pUC-ALD. Then mycobacterial plasmid pALD was created by ligating the 1.9 kb KpnI fragment containing the ald gene [SEQ ID NO:1] to KpnI-linearized pMD31 (Yu et al., 1998). The plasmid pALD was introduced by electroporation into *M. bovis* BCG, and recombinant *M. bovis* BCG selected on Middlebrook 7H9 agar (Difco) supplemented with 10% oleic/albumin/dextrose/catalase (OADC) enrichment and 25 µg/ml kanamycin.

Cloning of sdaA. Cloning of sdaA [SEQ ID NO:5] was accomplished in two steps. First, a 9.5 kb BamHI fragment of *M. tuberculosis* genomic DNA was ligated to BamHI-linearized pMD31 to generate pSDA1. Plasmid pSDAA was generated by cleavage of pSDA1 with PstI, followed by self-ligation of the 10.9 kb PstI fragment. The plasmid pSDAA was introduced by electroporation into *M. bovis* BCG, and recombinant *M. bovis* BCG selected on Middlebrook 7H9 agar (Difco) supplemented with 10% oleic/albumin/dextrose/catalase (OADC) enrichment and 25 μg/ml kanamycin.

EXAMPLE 1

Growth of BCG strains in Glycerol-Alanine-Salts (GAS) medium. During the course of our studies, we found that BCG-Japan strain was able to grow in GAS medium, albeit slower than in 7H9 medium. BCG-Frappier and BCG-Pasteur could not grow in GAS medium, even after prolonged incubation (2 months). The growth of other BCG strains in GAS medium was also examined. The results are summarized in Table I, and show that BCG-Japan, BCG-Russia, BCG-Moreau, BCG-Sweden and BCG-Birkhaug were able to grow in GAS medium while BCG-Frappier, BCG-Pasteur, BCG-Glaxo, BCG-Phipps, BCG-Tice, BCG-Denmark, and BCG-Prague could not. This is an interesting observation since all 12 BCG strains listed above were able to grow in 7H9 and Sauton broth medium (Table I). To find out why certain BCG strains were unable to grow in GAS medium, the chemical compositions of GAS, 7H9 and Sauton medium were compared. Supplementing $ZnSO_4$ (1 mg/liter), which is present in 7H9 and Sauton but not in GAS medium, or sodium pyruvate (0.5%), which is required for growth of large colonies of *M. bovis*, did not support the growth of BCG strains in GAS (data not shown). Next, nitrogen sources were compared. L-Asparagine (4 g/liter) is the only nitrogen source in Sauton medium while ammonium chloride (2 g/liter) and L-alanine (1 g/liter) are the main nitrogen sources in GAS. When L-asparagine (at 4 g per liter) was added to GAS medium, BCG-Frappier, BCG-Pasteur, BCG-Glaxo, BCG-Phipps, BCG-Tice, BCG-Denmark, and BCG-Prague were able to grow rapidly (Table I). Supplementing L-aspartate, L-glutamine, or L-glutamate but not other types of amino acids to GAS medium also supported the growth of these BCG strains (Table I). These results show that the failure of certain BCG strains to grow in GAS medium is caused by their inability to utilize the nitrogen source present.

EXAMPLE 2

Amino acids as the nitrogen source for growth of BCG strains. The above result prompted us to examine the ability of BCG strains to utilize various types of amino acids as the only nitrogen source. Since GAS medium contains a small amount of Bacto Casitone (0.3 g/liter), which is a complex mixture of various amino acids and peptides, we chose Sauton medium, which is a defined medium, for this purpose. The L-asparagine in the original formula for Sauton medium was replaced individually by each type of amino acids at the same concentration (27 mM), and pH was adjusted to 7.0. Ammonium chloride at 27 mM or 1 mM as the only nitrogen source was also tested. Table II summarizes the results for three representative BCG strains, BCG-Japan, BCG-Pasteur, and BCG-Frappier. Consistent with the result in Table I, all three BCG strains grew rapidly when L-asparagine, L-aspartate, L-glutamine, or L-glutamate was used as the only nitrogen source. BCG-Japan was able to grow on cationic amino acids (e.g., L-arginine, L-lysine) while BCG-Pasteur and BCG-Frappier could not. More interestingly, none of the BCG strains were able to utilize L-alanine, L-serine, L-leucine, L-isoleucine, L-methioine, or L-glycine as the only nitrogen source, while other *Mycobacterium* species, including pathogenic *M. tuberculosis* and *M. avium*, and nonpathogenic *M. smegmatis*, were able grow on these amino acids. These results demonstrate that BCG vaccine strains utilize limited types of amino acids as the nitrogen source for growth; some BCG strains such as BCG-Pasteur or BCG-Frappier can grow only on 4 types of amino acids (Table II). Such a limitation is likely to restrict the ability of BCG to grow and persist in vivo (within the host).

EXAMPLE 3

L-Alanine, D-alanine, or L-serine inhibits the growth of BCG. One surprising finding from the above experiment was that all BCG strains are able to grow on ammonium chloride as the only nitrogen source at both low (1 mM) or high concentrations (27 mM) (Table II). This is contradictory to the result obtained in GAS medium, in which ammonium chloride at 37 mM does not support the growth of BCG-Pasteur and BCG-Frappier (Table I). Since GAS medium also contains L-alanine, and L-alanine is not utilized by BCG strains for growth (Table II), the only possible explanation is that L-alanine actually inhibits the growth of BCG strains. To prove this, a modified GAS medium, in which L-alanine was omitted, was made and the growth of BCG strains in this medium was examined. As predicted, BCG-Frappier and BCG-Pasteur, which are unable to grow in the original GAS medium containing L-alanine, grew rapidly in GAS without L-alanine (FIG. 3). BCG-Japan also grew more rapidly in this L-alanine free medium than in the original GAS medium (FIG. 3). The same results were obtained for the other nine BCG strains listed in this report.

To further confirm this result, increasing concentrations of L-alanine were added to Sauton medium containing ammonium chloride (5 g/liter) and the growth of BCG-Japan, BCG-Frappier and BCG-Pasteur was determined (FIG. 4). Strikingly, even at a very low concentration (0.25 mM), L-alanine completely inhibited the growth of BCG-Frappier and BCG-Pasteur. Although the growth inhibition of BCG-Japan was somewhat less severe, L-alanine at 0.5 mM significantly reduced its growth and at 8-16 mM the growth was completely inhibited (FIG. 4). Taken together, these results clearly demonstrate that L-alanine inhibits the growth of BCG strains. We further found that D-alanine also inhibits the growth of BCG strains. The presence of D-alanine in GAS medium stopped the growth of BCG-Pasteur and BCG-Frappier, and significantly reduced the growth of BCG-Japan (FIG. 5). Similarly, the presence of L-serine in GAS medium significantly inhibited the growth of BCG-Japan, BCG-Frappier, and BCG-Pasteur (FIG. 7).

EXAMPLE 4

Expressing L-alanine dehydrogenase [SEQ ID NO:1; SEQ ID NO:2] in BCG relieves the inhibition of BCG growth by L-alanine and D-alanine. Alanine is an excellent source of nitrogen for many Mycobacterium species including M. tuberculosis, M avium, and M. smegmatis. D-Alanine degradation begins with racemization to L-alanine, which is then broken down to ammonium and pyruvate by L-alanine dehydrogenase. Interestingly, a functional L-alanine dehydrogenase was detected in M. tuberculosis and M. smegmatis but not in BCG-Japan or BCG-Copenhagen (Andersen et al., 1992; Hutter and Dick, 1998). We did not detect L-alanine dehydrogenase activity in any of the BCG strains listed in this study (data not shown). The failure of BCG strains to utilize L- or D-alanine as the only nitrogen source for growth is due to the lack of a functional L-alanine dehydrogenase. To prove this, the ald gene [SEQ ID NO:1] coding for L-alanine dehydrogenase [SEQ ID NO:2] in the M. tuberculosis genome was cloned into a shuttle vector and transformed into BCG-Frappier and BCG-Pasteur. The resulting recombinant BCG strains were tested for their ability to grow in GAS medium containing L-alanine or D-alanine. Both recombinant strains, BCG-Frappier/ald and BCG-Pasteur/ald, grew rapidly in GAS medium containing either L-alanine or D-alanine (FIG. 6), while strains containing the cloning vector alone did not grow. This result shows that expression of a functional L-alanine dehydrogenase [SEQ ID NO:1; SEQ ID NO:2] in BCG strains relieves the growth inhibition of BCG by L-alanine and D-alanine.

EXAMPLE 5

Expressing L-serine dehydratase [SEQ ID NO:5; SEQ ID NO:6] in BCG relieves the inhibition of BCG growth by L-serine. L-Serine is used by *M. tuberculosis, M. avium* and *M. smegmatis*, but not *M. bovis* BCG, as the only nitrogen for growth. The failure of BCG to utilize L-serine as the only nitrogen source is likely to be caused by either mutations on or altered expression of the gene encoding L-serine dehydratase, sdaA [SEQ ID NO:5], in BCG. Expression of sdaA [SEQ ID NO:5; SEQ ID NO:6] of *M. tuberculosis* in BCG allows BCG strains to grow on L-serine as the only nitrogen source and relieves the inhibition of BCG growth by L-serine (FIG. 8).

EXAMPLE 6

Inhibition of BCG growth by L-alanine, D-alanine and L-serine are likely to occur by blocking the activity of glutamine synthetase [SEQ ID NO:7] to [SEQ ID NO:14]. Glutamine synthetase plays a central role in nitrogen metabolism in bacteria (Reitzer, 1996). Working in tandem with glutamate synthase, glutamine synthetase catalyzes the synthesis of glutamine and glutamate, which together provide nitrogen for almost all amino acids, proteins, and nucleotides. In *Escherichia coli* and *Klebsiella aerogenes*, glutamine synthetase is under feedback inhibition—purified glutamine synthetase is inhibited by L-alanine, L-serine and glycine (Reitzer, 1996). Glutamine synthetase was identified as an extracellular protein in *M. tuberculosis* and *M. bovis* BCG (Harth et al., 1994). It is likely that undegraded L-alanine inhibits glutamine synthetase and subsequently prevents the growth of BCG. If this were correct, then L-serine, which was not catabolized by BCG for growth (Table I), would also inhibit the growth of BCG by the same mechanism. Supporting this hypothesis, addition of L-serine to GAS medium containing only ammonium chloride as the nitrogen source inhibits the growth of BCG-Frappier, BCG-Pasteur or BCG-Japan (FIG. 7). Furthermore, if glutamine synthetase were the target of L-alanine and L-serine inhibition, then supplementing amino acids that can be converted to glutamate would also alleviate their effects, as demonstrated in *K. aerogenes* (Janes and Bender, 1998). Indeed, addition of L-glutamate and amino acids that could be catabolized to yield glutamate (L-glutamine, L-asparagine, and L-aspartate) allows the growth of BCG strains in the presence of alanine (Table I), but those that could not be catabolized to glutamate (e.g., L-lysine, L-methioine, L-leucine) fail to allow growth. BCG-Frappier and BCG-Pasteur are more sensitive than BCG-Japan to inhibition by alanine and serine, this is due to differences in the expression level or activity of glutamine synthetase [SEQ ID NO:7] to [SEQ ID NO:14], i.e., BCG-Japan produces more glutamine synthetase or with higher activity than BCG-Frappier or BCG-Pasteur.

The present invention has been described in detail and with particular reference to the preferred embodiments; however, it will be understood by one having ordinary skill in the art that changes can be made without departing from the spirit and scope thereof. For example, where the application refers to proteins, it is clear that peptides and polypeptides may often be used. Likewise, where a gene is described in the application, it is clear that nucleic acids or gene fragments may often be used.

All publications (including Genbank entries), patents and patent applications are incorporated by reference in their entirety to the same extent as if each individual publication, patent or patent application was specifically and individually indicated to be incorporated by reference in its entirety.

TABLE I

| | Comparative growth of *M. tuberculosis*, *M. smegmatis* and *M. bovis* BCG substrains in 7H9, Sauton, and glycerol-alanine-salts (GAS) medium. | | | | | | |
|---|---|---|---|---|---|---|---|
| Mycobacterium[a] | 7H9 | Sauton | GAS | GAS + L-Asn[b] | GAS + L-Asp[b] | GAS + L-Glu[b] | GAS + L-Gln[b] |
| *M. tuberculosis*[c] | + | + | + | + | + | + | + |
| *M. smegmatis* | + | + | + | + | + | + | + |
| BCG-Russia | + | + | + | + | + | + | + |
| BCG-Moreau | + | + | + | + | + | + | + |
| BCG-Japan | + | + | + | + | + | + | + |
| BCG-Sweden | + | + | + | + | + | + | + |
| BCG-Birkhaug | + | + | + | + | + | + | + |
| BCG-Prague | + | + | − | + | + | + | + |
| BCG-Glaxo | + | + | − | + | + | + | + |
| BCG-Denmark | + | + | − | + | + | + | + |
| BCG-Tice | + | + | − | + | + | + | + |
| BCG-Frappier | + | + | − | + | + | + | + |

TABLE I-continued Comparative growth of M. tuberculosis, M. smegmatis and M. bovis BCG substrains in 7H9, Sauton, and glycerol-alanine-salts (GAS) medium.

| Mycobacterium[a] | 7H9 | Sauton | GAS | GAS + L-Asn[b] | GAS + L-Asp[b] | GAS + L-Glu[b] | GAS + L-Gln[b] |
|---|---|---|---|---|---|---|---|
| BCG-Phipps | + | + | − | + | + | + | + |
| BCG-Pasteur | + | + | − | + | + | + | + |

[a]Each 5 ml culture inoculated with 1 × 10$^7$ cells of M. smegmatis or M. bovis BCG substrains.
[b]L-Asn, L-Asp, L-Glu and L-Gln in GAS supplemented to a final concentration of 27 mM.
[c]Based on research literature.

TABLE II

Comparative growth of M. bovis BCG-Japan, BCG-Frappier, BCG-Pasteur, M. tuberculosis, M. avium and M. smegmatis

| Media[a] | BCG-Japan[b] | BCG-Frappier[b] | BCG-Pasteur[b] | M. tuberculosis[c] | M. avium[c] | M. smegmatis[b] |
|---|---|---|---|---|---|---|
| Sauton basal | − | − | − | − | − | − |
| Group 1 | | | | | | |
| Sauton + L-Asn | +++ | +++ | +++ | +++ | +++ | +++ |
| Sauton + L-Asp | +++ | +++ | +++ | +++ | +++ | +++ |
| Sauton + L-Glu | +++ | +++ | +++ | +++ | +++ | +++ |
| Sauton + L-Gln | +++ | +++ | +++ | +++ | +++ | +++ |
| Sauton + L-Cys | +++ | +++ | +++ | +++ | +++ | +++ |
| Sauton + NH$_4$Cl | +++ | +++ | +++ | +++ | +++ | +++ |
| Group 2 | | | | | | |
| Sauton + L-Arg | ++ | − | − | +++ | +++ | +++ |
| Sauton + L-His | ++ | − | − | +++ | +++ | +++ |
| Sauton + L-Lys | ++ | − | − | NA | +++ | +++ |
| Sauton + L-Pro | ++ | − | − | NA | − | +++ |
| Sauton + GABA | ++ | − | − | NA | NA | +++ |
| Sauton + L-Ornithine | ++ | − | − | NA | NA | +++ |
| Group 3 | | | | | | |
| Sauton + L-Ala | − | − | − | +++ | +++ | +++ |
| Sauton + L-Ser | − | − | − | +++ | +++ | +++ |
| Sauton + L-Leu | − | − | − | +++ | +++ | +++ |
| Sauton + L-Ile | − | − | − | +++ | +++ | +++ |
| Sauton + L-Met | − | − | − | NA | +++ | +++ |
| Sauton + Glycine | − | − | − | +++ | NA | +++ |
| Group 4 | | | | | | |
| Sauton + L-Trp | − | − | − | − | − | − |
| Sauton + L-Phe | − | − | − | +++ | − | − |
| Sauton + L-Tyr | − | − | − | − | − | − |
| Sauton + L-Val | − | − | − | NA | − | − |
| Sauton + L-Thr | − | − | − | NA | − | − |

[a]All amino acids, L-Ornithine and GABA supplemented to final concentration of 27 mM. NH$_4$Cl was tested at 1 mM, 27 mM and 96 mM.
[b]Each 5 ml culture inoculated with 1 × 10$^7$ cells of M. smegmatis or M. bovis BCG substrains.
[c]Based on research literature.

REFERENCE

Andersen, A. B. F., P. F. Andersen, and L. Ljungqvist. 1992. Structure and function of a 40,000-molecular-weight protein antigen of *Mycobacterium tuberculosis*. *Infect. Immun.* 60:2317-23.

Andersen, P. 2001. TB vaccines: progress and problems. *Trends Immunol.* 22:160-8.

Baldwin, S. L. F., C. F. D'Souza, A. D. F. Roberts, B. P. F. Kelly, A. A. F. Frank, M. A. F. Lui, J. B. F. Ulmer, K. F. Huygen, D. M. F. McMurray, and I. M. Orme. 1998. Evaluation of new vaccines in the mouse and guinea pig model of tuberculosis. *Infect. Immun.* 66:2951-9.

Behr, M. A. F., M. A. F. Wilson, W. P. F. Gill, H. F. Salamon, G. K. F. Schoolnik, S. F. Rane, and P. M. Small. 1999. Comparative genomics of BCG vaccines by whole-genome DNA microarray. *Science* 284:1520-3.

Brandt, L., C. J. Feino, O. A. Weinreich, B. Chilima, P. Hirsch, R. Appelberg, and P. Andersen. 2002. Failure of the *Mycobacterium bovis* BCG Vaccine: Some Species of Environmental *Mycobacteria* Block Multiplication of BCG and Induction of Protective Immunity to Tuberculosis. *Infect. Immun.* 70:672-678.

Barclay, R. and P. R. Wheeler. 1989. Metabolism of mycobacterium in tissues, p. 37-106. In C. Ratledge, J. Stanford, and J. M. Grange (ed.), Clinical aspects of mycobacterial disease. Academic Press, London, United Kingdom.

Brosch, R. F., S. V. F. Gordon, C. F. Buchrieser, A. S. F. Pym, T. F. Garnier, and S. T. Cole. 2000. Comparative genomics uncovers large tandem chromosomal duplications in *Mycobacterium bovis* BCG Pasteur. *Yeast* 17:111-23.

Colditz, G. A. F., T. F. F. Brewer, C. S. F. Berkey, M. E. F. Wilson, E. F. Burdick, H. V. F. Fineberg, and F. Mosteller. 1994. Efficacy of BCG vaccine in the prevention of tuberculosis. Meta-analysis of the published literature. *JAMA* 271:698-702.

de Boer, E. C., Bevers, R. F., Kurth, K. H., and Schamhart, D. H. 1996. Double fluorescent flow cytometric assessment of bacterial internalization and binding by epithelial cells. *Cytometry.* 25:381-387.

Dunn, P. L. F. and R. J. North. 1995. Virulence ranking of some *Mycobacterium tuberculosis* and *Mycobacterium bovis* strains according to their ability to multiply in the lungs, induce lung pathology, and cause mortality in mice. *Infect. Immun.* 63:3428-37.

Fine, P. E. 1995. Variation in protection by BCG: implications of and for heterologous immunity. *Lancet* 346:1339-45.

Fine, P. E. 1989. The BCG story: lessons from the past and implications for the future. *Rev. Infect. Dis.* 11:S353-9.

Fine, P. E. F. and E. Vynnycky. 1998. The effect of heterologous immunity upon the apparent efficacy of (e.g. BCG) vaccines. *Vaccine* 16:1923-8.

Fritz, C. F., S. F. Maass, A. F. Kreft, and F. C. Bange. 2002. Dependence of *Mycobacterium bovis* BCG on anaerobic nitrate reductase for persistence is tissue specific. *Infect. Immun.* 70:286-91.

Harth, G. F., P. C. F. Zamecnik, J. Y. F. Tang, D. F. Tabatadze, and M. A. Horwitz. 2000. Treatment of *Mycobacterium tuberculosis* with antisense oligonucleotides to glutamine synthetase mRNA inhibits glutamine synthetase activity, formation of the poly-L-glutamate/glutamine cell wall structure, and bacterial replication. *Proc. Natl. Acad. Sci. USA* 97:418-23.

Harth, G. F., D. L. F. Clemens, and M. A. Horwitz. 1994. Glutamine synthetase of *Mycobacterium tuberculosis*: extracellular release and characterization of its enzymatic activity. *Proc. Natl. Acad. Sci. USA* 91:9342-6.

Hogan, L. H. F., W. F. Markofski, A. F. Bock, B. F. Barger, J. D. F. Morrissey, and M. Sandor. 2001. *Mycobacterium bovis* BCG-induced granuloma formation depends on gamma interferon and CD40 ligand but does not require CD28. *Infect. Immun.* 69:2596-603.

Hutter, B. F. and M. Singh. 1999. Properties of the 40 kDa antigen of *Mycobacterium tuberculosis*, a functional L-alanine dehydrogenase. *Biochem. J.* 343:669-72.

Hutter, B. F. and T. Dick. 1998. Increased alanine dehydrogenase activity during dormancy in *Mycobacterium smegmatis. FEMS Microbiol. Lett.* 167:7-11.

Janes, B. K. F. and R. A. Bender. 1998. Alanine catabolism in *Klebsiella aerogenes*: molecular characterization of the dadAB operon and its regulation by the nitrogen assimilation control protein. *J. Bacteriol.* 180:563-70.

Lagranderie, M. R. F., A. M. F. Balazuc, E. F. Deriaud, C. D. F. Leclerc, and M. Gheorghiu. 1996. Comparison of immune responses of mice immunized with five different *Mycobacterium bovis* BCG vaccine strains. *Infect. Immun.* 64:1-9.

Lamm, D. L. 2000. Efficacy and safety of bacille Calmette-Guerin immunotherapy in superficial bladder cancer. *Clin. Infect. Dis.* 31 (Suppl 3):S86-90.

Lockyer, C. R., and Gilatt, D. A. 2001. BCG immunotherapy for superficial bladder cancer. *J. R. Soc. Med.* 94:119-23.

McKinney, J. D. F., z. B. Honer, E. J. F. Munoz-Elias, A. F. Miczak, B. F. Chen, W. T. F. Chan, D. F. Swenson, J. C. F. Sacchettini, W. R. J. Jacobs, and D. G. Russell. 2000. Persistence of *Mycobacterium tuberculosis* in macrophages and mice requires the glyoxylate shunt enzyme isocitrate lyase. *Nature* 406:735-8.

Moisan, J. F., W. F. Wojciechowski, C. F. Guilbault, C. F. Lachance, S. Di Marco, E. F. Skamene, G. F. Matlashewski, and D. Radzioch. 2001.Clearance of infection with *Mycobacterium bovis* BCG in mice is enhanced by treatment with S28463 (R-848), and its efficiency depends on expression of wild-type Nramp1 (resistance allele).—*Antimicrob. Agents Chemother.* 45:3059-64.

Oettinger, T. F., M. F. Jorgensen, A. F. Ladefoged, K. F. Haslov, and P. Andersen. 1999. Development of the *Mycobacterium bovis* BCG vaccine: review of the historical and biochemical evidence for a genealogical tree. *Tuber. Lung Dis.* 79:243-50.

Orme, I. M. 2001. The search for new vaccines against tuberculosis. *J. Leukoc. Biol.* 70:1-10.

Prescott, S., Jackson, A. M., Hawkyard, S. J., Alexandroff, A. B., and James, K. 2000. Mechanisms of action of intravesical bacille Calmette-Guerin: local immune mechanisms. *Clin. Infect. Dis.* 31 (Suppl 3):S91-3.

Reitzer, L. J. 1996. Ammonium assimilation and the biosynthesis of glutamine, glutamate, aspartate, asparagine, L-alanine, and D-alanine, p. 380-390. In Neidhardt, F. C. (ed.), *Escherichia coli and Salmonella*, ASM Press, Washington, D.C.

Sterne, J. A., L. C. Rodrigues, and I. N. Guedes. 1998. Does the efficacy of BCG decline with time since vaccination? *International Journal of Tuberculosis & Lung Disease* 2:200-207.

Young, D. B. 2000. Current tuberculosis vaccine development. *Clin. Infect. Dis.* 30:S254-6.

Yu, S. F., E. F. Fiss, and W. R. J. Jacobs. 1998. Analysis of the exochelin locus in *Mycobacterium smegmatis*: biosynthesis genes have homology with genes of the peptide synthetase family. *J. Bacteriol.* 180:4676-85.

We claim:

1. A live recombinant *Mycobacterium bovis*-BCG strain comprising a heterologous nucleic acid capable of expression, the heterologous nucleic acid encoding at least one protein or polypeptide that exhibits alanine dehydrogenase activity, glutamine synthetase activity, or L-serine dehydratase activity.

2. The live recombinant *Mycobacterium bovis*-BCG strain of claim 1, wherein the at least one protein or polypeptide is selected from the group consisting of alanine dehydrogenase [SEQ ID NO:1; SEQ ID NO:2], glutamine synthetase [SEQ ID NO:7 to SEQ ID NO:14] and L-serine dehydratase [SEQ ID NO:5; SEQ ID NO:6].

3. The live recombinant *Mycobacterium bovis*-BCG strain of claim 1, wherein the nucleic acid comprises all or part of at least one nucleic acid molecule selected from the group consisting of [SEQ ID NO:1], [SEQ ID NO:5], [SEQ ID NO:7], [SEQ ID NO:9], [SEQ ID NO:11], and [SEQ ID NO:13].

4. The live recombinant *Mycobacterium bovis*-BCG strain of claim 1, wherein the nucleic acid comprises a sequence having at least 60% sequence identity to at least one nucleic acid molecule selected from the group consisting of [SEQ ID NO:1], [SEQ ID NO:5], [SEQ ID NO:7], [SEQ ID NO:9], [SEQ ID NO:11] and [SEQ ID NO:13].

5. The live recombinant *Mycobacterium bovis*-BCG strain of claim 3, wherein the nucleic acid molecule has undergone modification.

6. The live recombinant *Mycobacterium bovis*-BCG strain of claim 1, wherein the *Mycobacterium bovis*-BCG strain is selected from the group consisting of *Mycobacterium bovis*-BCG-Russia, *Mycobacterium bovis*-BCG-Moreau, *Mycobacterium bovis*-BCG-Japan, *Mycobacterium bovis*-BCG-Sweden, *Mycobacterium bovis*-BCG-Birkhaug, *Mycobacterium bovis*-BCG-Prague, *Mycobacterium bovis*-BCG-Glaxo, *Mycobacterium bovis*-BCG-Den mark, *Mycobacterium bovis*-BCG-Tice, *Mycobacterium bovis*-BCG-Frappier, *Mycobacterium bovis*-BCG-Connaught, *Mycobacterium bovis*-BCG-Phipps, and *Mycobacterium bovis*-BCG-Pasteur.

7. A pharmaceutical composition comprising the live recombinant *Mycobacterium bovis*-BCG strain of claim 1.

8. A vaccine or immunogenic composition for treatment or prophylaxis of a mammal against challenge by *Mycobacterium tuberculosis* or *Mycobacterium bovis* comprising the live recombinant *Mycobacterium bovis*-BCG strain of claim 1.

9. The vaccine or immunogenic composition of claim 8, further comprising a pharmaceutically acceptable carrier.

10. The vaccine or immunogenic composition of claim 8, further comprising an adjuvant.

11. The vaccine or immunogenic composition of claim 8, further comprising immunogenic materials from one or more other pathogens.

12. A method for treatment or prophylaxis of a mammal against challenge by *Mycobacterium tuberculosis* or *Mycobacterium bovis* comprising administering to the mammal the live recombinant *Mycobacterium bovis*-BCG strain of claim 1.

13. The method of claim 12, wherein the mammal is a cow.

14. The method of claim 12, wherein the mammal is a human.

15. The method of claim 12, wherein the vaccine or immunogenic composition is administered in the presence of an adjuvant.

16. A method for treatment or prophylaxis of a mammal against cancer comprising administering to the mammal the live recombinant *Mycobacterium bovis*-BCG strain of claim 1.

17. The method of claim 16, wherein the vaccine or immunogenic composition is administered in the presence of an adjuvant.

18. The method of claim 16, wherein the cancer is bladder cancer.

19. A test kit comprising the live recombinant *Mycobacterium bovis*-BCG strain of claim 1.

20. A medium composition for inhibiting the growth of *Mycobacterium bovis*-BCG comprising alanine or serine as the only nitrogen source for growth.

21. The medium composition of claim 20, further comprising:
   (a) a carbon source;
   (b) iron;
   (c) magnesium; and
   (d) $SO_4$.

22. A medium composition of claim 21, wherein the carbon source is selected from the group consisting of glycerol, dextrose, citrate and glucose.

23. A method of culturing *Mycobacterium bovis*-BCG comprising:
   (a) obtaining a sample of *Mycobacterium bovis*-BCG; and
   (b) culturing the sample in a medium comprising histidine.

24. The live recombinant *Mycobacterium bovis*-BCG strain of claim 4, wherein the nucleic acid molecule has undergone modification.

* * * * *

UNITED STATES PATENT AND TRADEMARK OFFICE
CERTIFICATE OF CORRECTION

PATENT NO. : 7,611,720 B2
APPLICATION NO. : 10/511718
DATED : November 3, 2009
INVENTOR(S) : Liu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 611 days.

Signed and Sealed this

Twelfth Day of October, 2010

David J. Kappos
*Director of the United States Patent and Trademark Office*

SEQUENCE LISTING

```
<160> NUMBER OF SEQ ID NOS: 14

<210> SEQ ID NO 1
<211> LENGTH: 1116
<212> TYPE: DNA
<213> ORGANISM: Mycobacterium tuberculosis
<220> FEATURE:
<221> NAME/KEY: CDS
<222> LOCATION: (1)..(1116)
<223> OTHER INFORMATION: Sequence is identical to GenBank entries GI:
      3089350 and MTU92472
```

<400> SEQUENCE: 1

```
atg cgc gtc ggt att ccg acc gag acc aaa aac aac gaa ttc cgg gtg       48
Met Arg Val Gly Ile Pro Thr Glu Thr Lys Asn Asn Glu Phe Arg Val
 1               5                  10                  15 gcc atc acc ccg gcc ggc gtc gcg gaa cta acc cgt cgt ggc cat gag       96
Ala Ile Thr Pro Ala Gly Val Ala Glu Leu Thr Arg Arg Gly His Glu
                20                  25                  30 gtg ctc atc cag gca ggt gcc gga gag ggc tcg gct atc acc gac gcg      144
Val Leu Ile Gln Ala Gly Ala Gly Glu Gly Ser Ala Ile Thr Asp Ala
             35                  40                  45 gat ttc aag gcg gca ggc gcg caa ctg gtc ggc acc gcc gac cag gtg      192
Asp Phe Lys Ala Ala Gly Ala Gln Leu Val Gly Thr Ala Asp Gln Val
 50                  55                  60 tgg gcc gac gct gat tta ttg ctc aag gtc aaa gaa ccg ata gcg gcg      240
Trp Ala Asp Ala Asp Leu Leu Leu Lys Val Lys Glu Pro Ile Ala Ala
 65                  70                  75                  80 gaa tac ggc cgc ctg cga cac ggg cag atc ttg ttc acg ttc ttg cat      288
Glu Tyr Gly Arg Leu Arg His Gly Gln Ile Leu Phe Thr Phe Leu His
                 85                  90                  95 ttg gcc gcg tca cgt gct tgc acc gat gcg ttg gat tcc ggc acc          336
Leu Ala Ala Ser Arg Ala Cys Thr Asp Ala Leu Leu Asp Ser Gly Thr
                100                 105                 110 acg tca att gcc tac gag acc gtc cag acc gcc gac ggc gca cta ccc      384
Thr Ser Ile Ala Tyr Glu Thr Val Gln Thr Ala Asp Gly Ala Leu Pro
            115                 120                 125 ctg ctt gcc ccg atg agc gaa gtc gcc ggt cga ctc gcc gcc cag gtt      432
Leu Leu Ala Pro Met Ser Glu Val Ala Gly Arg Leu Ala Ala Gln Val
130                 135                 140 ggc gct tac cac ctg atg cga acc caa ggg ggc cgc ggt gtg ctg atg      480
Gly Ala Tyr His Leu Met Arg Thr Gln Gly Gly Arg Gly Val Leu Met
145                 150                 155                 160 ggc ggg gtg ccc ggc gtc gaa ccg gcc gac gtc gtg gtg atc ggc gcc      528
Gly Gly Val Pro Gly Val Glu Pro Ala Asp Val Val Val Ile Gly Ala
                165                 170                 175 ggc acc gcc ggc tac aac gca gcc cgc atc gcc aac ggc atg ggc gcg      576
Gly Thr Ala Gly Tyr Asn Ala Ala Arg Ile Ala Asn Gly Met Gly Ala
            180                 185                 190 acc gtt acg gtt cta gac atc aac atc gac aaa ctt cgg caa ctc gac      624
Thr Val Thr Val Leu Asp Ile Asn Ile Asp Lys Leu Arg Gln Leu Asp
        195                 200                 205 gcc gag ttc tgc ggc cgg atc cac act cgc tac tca tcg gcc tac gag      672
Ala Glu Phe Cys Gly Arg Ile His Thr Arg Tyr Ser Ser Ala Tyr Glu
    210                 215                 220 ctc gag ggt gcc gtc aaa cgt gcc gac ctg gtg att ggg gcc gtc ctg      720
Leu Glu Gly Ala Val Lys Arg Ala Asp Leu Val Ile Gly Ala Val Leu
225                 230                 235                 240 gtg cca ggc gcc aag gca ccc aaa tta gtc tcg aat tca ctt gtc gcg      768
Val Pro Gly Ala Lys Ala Pro Lys Leu Val Ser Asn Ser Leu Val Ala
                245                 250                 255 cat atg aaa cca ggt gcg gta ctg gtg gat ata gcc atc gac cag ggc      816
His Met Lys Pro Gly Ala Val Leu Val Asp Ile Ala Ile Asp Gln Gly
            260                 265                 270 ggc tgt ttc gaa ggc tca cga ccg acc acc tac gac cac ccg acg ttc      864
Gly Cys Phe Glu Gly Ser Arg Pro Thr Thr Tyr Asp His Pro Thr Phe
        275                 280                 285 gcc gtg cac gac acg ctg ttt tac tgc gtg gcg aac atg ccc gcc tcg      912
Ala Val His Asp Thr Leu Phe Tyr Cys Val Ala Asn Met Pro Ala Ser
    290                 295                 300
```

-continued

```
gtg ccg aag acg tcg acc tac gcg ctg acc aac gcg acg atg ccg tat    960
Val Pro Lys Thr Ser Thr Tyr Ala Leu Thr Asn Ala Thr Met Pro Tyr
305             310                 315                 320 gtg ctc gag ctt gcc gac cat ggc tgg cgg gcg gcg tgc cgg tcg aat   1008
Val Leu Glu Leu Ala Asp His Gly Trp Arg Ala Ala Cys Arg Ser Asn
            325                 330                 335 ccg gca cta gcc aaa ggt ctt tcg acg cac gaa ggg gcg tta ctg tcc   1056
Pro Ala Leu Ala Lys Gly Leu Ser Thr His Glu Gly Ala Leu Leu Ser
        340                 345                 350 gaa cgg gtg gcc acc gac ctg ggg gtg ccg ttc acc gag ccc gcc agc   1104
Glu Arg Val Ala Thr Asp Leu Gly Val Pro Phe Thr Glu Pro Ala Ser
    355                 360                 365 gtg ctg gcc tga                                                   1116
Val Leu Ala
    370

<210> SEQ ID NO 2
<211> LENGTH: 371
<212> TYPE: PRT
<213> ORGANISM: Mycobacterium tuberculosis
<220> FEATURE:
<221> NAME/KEY:
<222> LOCATION:
<223> OTHER INFORMATION: Sequence is identical to SwissProt entry SP:
      DHA_MYCTU

<400> SEQUENCE: 2

Met Arg Val Gly Ile Pro Thr Glu Thr Lys Asn Asn Glu Phe Arg Val
1               5                   10                  15

Ala Ile Thr Pro Ala Gly Val Ala Glu Leu Thr Arg Arg Gly His Glu
            20                  25                  30

Val Leu Ile Gln Ala Gly Ala Gly Glu Gly Ser Ala Ile Thr Asp Ala
        35                  40                  45

Asp Phe Lys Ala Ala Gly Ala Gln Leu Val Gly Thr Ala Asp Gln Val
    50                  55                  60

Trp Ala Asp Ala Asp Leu Leu Leu Lys Val Lys Glu Pro Ile Ala Ala
65                  70                  75                  80

Glu Tyr Gly Arg Leu Arg His Gly Gln Ile Leu Phe Thr Phe Leu His
                85                  90                  95

Leu Ala Ala Ser Arg Ala Cys Thr Asp Ala Leu Leu Asp Ser Gly Thr
            100                 105                 110

Thr Ser Ile Ala Tyr Glu Thr Val Gln Thr Ala Asp Gly Ala Leu Pro
        115                 120                 125

Leu Leu Ala Pro Met Ser Glu Val Ala Gly Arg Leu Ala Ala Gln Val
    130                 135                 140

Gly Ala Tyr His Leu Met Arg Thr Gln Gly Gly Arg Gly Val Leu Met
145                 150                 155                 160

Gly Gly Val Pro Gly Val Glu Pro Ala Asp Val Val Ile Gly Ala
                165                 170                 175

Gly Thr Ala Gly Tyr Asn Ala Ala Arg Ile Ala Asn Gly Met Gly Ala
            180                 185                 190

Thr Val Thr Val Leu Asp Ile Asn Ile Asp Lys Leu Arg Gln Leu Asp
        195                 200                 205

Ala Glu Phe Cys Gly Arg Ile His Thr Arg Tyr Ser Ser Ala Tyr Glu
    210                 215                 220

Leu Glu Gly Ala Val Lys Arg Ala Asp Leu Val Ile Gly Ala Val Leu
225                 230                 235                 240

Val Pro Gly Ala Lys Ala Pro Lys Leu Val Ser Asn Ser Leu Val Ala
```

-continued

```
                245                 250                 255
His Met Lys Pro Gly Ala Val Leu Val Asp Ile Ala Ile Asp Gln Gly
            260                 265                 270

Gly Cys Phe Glu Gly Ser Arg Pro Thr Thr Tyr Asp His Pro Thr Phe
        275                 280                 285

Ala Val His Asp Thr Leu Phe Tyr Cys Val Ala Asn Met Pro Ala Ser
    290                 295                 300

Val Pro Lys Thr Ser Thr Tyr Ala Leu Thr Asn Ala Thr Met Pro Tyr
305                 310                 315                 320

Val Leu Glu Leu Ala Asp His Gly Trp Arg Ala Ala Cys Arg Ser Asn
                325                 330                 335

Pro Ala Leu Ala Lys Gly Leu Ser Thr His Glu Gly Ala Leu Leu Ser
            340                 345                 350

Glu Arg Val Ala Thr Asp Leu Gly Val Pro Phe Thr Glu Pro Ala Ser
        355                 360                 365

Val Leu Ala
    370

<210> SEQ ID NO 3
<211> LENGTH: 399
<212> TYPE: DNA
<213> ORGANISM: Mycobacterium bovis
<220> FEATURE:
<221> NAME/KEY: CDS
<222> LOCATION: (1)..(399)

<400> SEQUENCE: 3 atg cgc gtc ggt att ccg acc gag acc aaa aac aac gaa ttc cgg gtg      48
Met Arg Val Gly Ile Pro Thr Glu Thr Lys Asn Asn Glu Phe Arg Val
1               5                   10                  15 gcc atc acc ccg gcc ggc gtc gcg gaa cta acc cgt cgt ggc cat gag      96
Ala Ile Thr Pro Ala Gly Val Ala Glu Leu Thr Arg Arg Gly His Glu
                20                  25                  30 gtg ctc atc cag gca ggt gcc gga gag ggc tcg gct atc acc gac gcg     144
Val Leu Ile Gln Ala Gly Ala Gly Glu Gly Ser Ala Ile Thr Asp Ala
            35                  40                  45 gat ttc aag gcg gca ggc gcg caa ctg gtc ggc acc gcc gac cag gtg     192
Asp Phe Lys Ala Ala Gly Ala Gln Leu Val Gly Thr Ala Asp Gln Val
        50                  55                  60 tgg gcc gac gct gat tta ttg ctc aag gtc aaa gaa ccg ata gcg gcg     240
Trp Ala Asp Ala Asp Leu Leu Leu Lys Val Lys Glu Pro Ile Ala Ala
65                  70                  75                  80 gaa tac ggc cgc ctg cga cac ggg cga tct tgt tca cgt tct tgc att     288
Glu Tyr Gly Arg Leu Arg His Gly Arg Ser Cys Ser Arg Ser Cys Ile
                85                  90                  95 tgg ccg cgt cac gtg ctt gca ccg atg cgt tgt tgg att ccg gca cca     336
Trp Pro Arg His Val Leu Ala Pro Met Arg Cys Trp Ile Pro Ala Pro
                100                 105                 110 cgt caa ttg cct acg aga ccg tcc aga ccg ccg acg gcg cac tac ccc     384
Arg Gln Leu Pro Thr Arg Pro Ser Arg Pro Pro Thr Ala His Tyr Pro
            115                 120                 125 tgc ttg ccc cga tga                                                  399
Cys Leu Pro Arg
130

<210> SEQ ID NO 4
<211> LENGTH: 132
<212> TYPE: PRT
<213> ORGANISM: Mycobacterium bovis
```

```
<400> SEQUENCE: 4

Met Arg Val Gly Ile Pro Thr Glu Thr Lys Asn Asn Glu Phe Arg Val
1               5                   10                  15

Ala Ile Thr Pro Ala Gly Val Ala Glu Leu Thr Arg Arg Gly His Glu
            20                  25                  30

Val Leu Ile Gln Ala Gly Ala Gly Glu Gly Ser Ala Ile Thr Asp Ala
        35                  40                  45

Asp Phe Lys Ala Ala Gly Ala Gln Leu Val Gly Thr Ala Asp Gln Val
    50                  55                  60

Trp Ala Asp Ala Asp Leu Leu Lys Val Lys Glu Pro Ile Ala Ala
65                  70                  75                  80

Glu Tyr Gly Arg Leu Arg His Gly Arg Ser Cys Ser Arg Ser Cys Ile
                85                  90                  95

Trp Pro Arg His Val Leu Ala Pro Met Arg Cys Trp Ile Pro Ala Pro
            100                 105                 110

Arg Gln Leu Pro Thr Arg Pro Ser Arg Pro Pro Thr Ala His Tyr Pro
        115                 120                 125

Cys Leu Pro Arg
    130

<210> SEQ ID NO 5
<211> LENGTH: 1386
<212> TYPE: DNA
<213> ORGANISM: Mycobacterium tuberculosis
<220> FEATURE:
<221> NAME/KEY: CDS
<222> LOCATION: (1)..(1386)
<223> OTHER INFORMATION: Sequence is identical to the complement of
      nucleotides 13172-14551 of GenBank entry GB:MTV030 [AL021428]
      Sequence is identical to the complement of nucleotides 13195-14580
      of GenBank entry GB:AE006919

<400> SEQUENCE: 5 atg acc atc agc gtc ttc gac ctg ttc acc atc ggc atc ggg ccg tcc      48
Met Thr Ile Ser Val Phe Asp Leu Phe Thr Ile Gly Ile Gly Pro Ser
1               5                   10                  15 agt tcc cac acc gtg gga ccg atg cgc gcg gca aac cag ttc gta gtt      96
Ser Ser His Thr Val Gly Pro Met Arg Ala Ala Asn Gln Phe Val Val
            20                  25                  30 gcg ctg cgc cgc cgg ggc cac ctg gat gac ctc gag gcg atg cga gtg     144
Ala Leu Arg Arg Arg Gly His Leu Asp Asp Leu Glu Ala Met Arg Val
        35                  40                  45 gat ctg ttc ggc tcg ctc gcg gcc acc gga gcc ggt cat ggc acc atg     192
Asp Leu Phe Gly Ser Leu Ala Ala Thr Gly Ala Gly His Gly Thr Met
    50                  55                  60 tcg gcg ata ttg ctg ggg ctg gaa ggc tgc cag cca gaa acg att acc     240
Ser Ala Ile Leu Leu Gly Leu Glu Gly Cys Gln Pro Glu Thr Ile Thr
65                  70                  75                  80 acc gaa cac aag gaa cgc cgg ctc gcc gag atc gca gcg tcc ggc gtg     288
Thr Glu His Lys Glu Arg Arg Leu Ala Glu Ile Ala Ala Ser Gly Val
                85                  90                  95 acg cga atc ggc ggt gtc att ccg gtc ccg ctg acc gag cgt gat atc     336
Thr Arg Ile Gly Gly Val Ile Pro Val Pro Leu Thr Glu Arg Asp Ile
            100                 105                 110 gac ctg cat ccc gac atc gtt ctg cca acg cat ccc aac gga atg acg     384
Asp Leu His Pro Asp Ile Val Leu Pro Thr His Pro Asn Gly Met Thr
        115                 120                 125 ttc act gcc gcg ggc cca cac ggc cgc gtc ttg gcc acc gag act tat     432
Phe Thr Ala Ala Gly Pro His Gly Arg Val Leu Ala Thr Glu Thr Tyr
    130                 135                 140
```

-continued

| | |
|---|---|
| ttt tcg gtg ggc gga ggg ttc atc gtc acg gaa cag acc agc ggc aac<br>Phe Ser Val Gly Gly Gly Phe Ile Val Thr Glu Gln Thr Ser Gly Asn<br>145                150              155              160 | 480 |
| agc ggc caa cat cca tgc tca gtt gcc ctt ccc tac gtg tcg gcc caa<br>Ser Gly Gln His Pro Cys Ser Val Ala Leu Pro Tyr Val Ser Ala Gln<br>                165              170              175 | 528 |
| gaa ctg ctg gac atc tgt gac cgc ctc gac gtg tca att agc gaa gcg<br>Glu Leu Leu Asp Ile Cys Asp Arg Leu Asp Val Ser Ile Ser Glu Ala<br>         180               185              190 | 576 |
| gcg ctg cgc aac gaa aca tgt tgc cgc acc gag aac gag gta cgc gcc<br>Ala Leu Arg Asn Glu Thr Cys Cys Arg Thr Glu Asn Glu Val Arg Ala<br>195                200              205 | 624 |
| gcg ctg ctg cac ctg cgc gac gtc atg gtt gag tgc gaa cag cgg agc<br>Ala Leu Leu His Leu Arg Asp Val Met Val Glu Cys Glu Gln Arg Ser<br>    210                215              220 | 672 |
| atc gct cgc gaa ggg ttg ctt cct ggc ggc ctc cgg gtg cgc cgg cga<br>Ile Ala Arg Glu Gly Leu Leu Pro Gly Gly Leu Arg Val Arg Arg Arg<br>225                230              235              240 | 720 |
| gcg aag gtg tgg tat gac cgc ttg aac gcc gaa gac ccc act cgc aag<br>Ala Lys Val Trp Tyr Asp Arg Leu Asn Ala Glu Asp Pro Thr Arg Lys<br>                245              250              255 | 768 |
| ccg gaa ttc gct gag gac tgg gtc aac ctg gtc gcg ctg gca gtc aac<br>Pro Glu Phe Ala Glu Asp Trp Val Asn Leu Val Ala Leu Ala Val Asn<br>         260               265              270 | 816 |
| gag gag aac gcc tcc ggt ggg cgc gtc gtc acc gcc ccg acc aac ggt<br>Glu Glu Asn Ala Ser Gly Gly Arg Val Val Thr Ala Pro Thr Asn Gly<br>275                280              285 | 864 |
| gcc gcc ggc atc gtg ccg gcg gtc ctg cac tac gca atc cac tac acg<br>Ala Ala Gly Ile Val Pro Ala Val Leu His Tyr Ala Ile His Tyr Thr<br>    290                295              300 | 912 |
| tcg gcc ggc gcg ggg gac ccc gac gat gtc acc gtg cga ttc ctg ctc<br>Ser Ala Gly Ala Gly Asp Pro Asp Asp Val Thr Val Arg Phe Leu Leu<br>305                310              315              320 | 960 |
| act gct gga gcc atc gga tcg ttg ttc aag gag cga gca tcg atc tcc<br>Thr Ala Gly Ala Ile Gly Ser Leu Phe Lys Glu Arg Ala Ser Ile Ser<br>                325              330              335 | 1008 |
| gga gcc gag gtc ggc tgt cag ggc gag gtc ggc tcc gcg gcc gcc atg<br>Gly Ala Glu Val Gly Cys Gln Gly Glu Val Gly Ser Ala Ala Ala Met<br>         340               345              350 | 1056 |
| gcc gcc gcc gga ttg gct gaa atc ctc ggc ggc aca ccg cga caa gtg<br>Ala Ala Ala Gly Leu Ala Glu Ile Leu Gly Gly Thr Pro Arg Gln Val<br>             355               360              365 | 1104 |
| gaa aac gcc gcc gag atc gcc atg gaa cac agc ctc ggc ctg acc tgt<br>Glu Asn Ala Ala Glu Ile Ala Met Glu His Ser Leu Gly Leu Thr Cys<br>370                375              380 | 1152 |
| gac ccc atc gcc ggg ctg gtg cag atc ccc tgc atc gaa cgc aac gcg<br>Asp Pro Ile Ala Gly Leu Val Gln Ile Pro Cys Ile Glu Arg Asn Ala<br>385                390              395              400 | 1200 |
| att tcc gcc ggc aag gcc atc aac gcc gca cgg atg gca ttg cgc ggc<br>Ile Ser Ala Gly Lys Ala Ile Asn Ala Ala Arg Met Ala Leu Arg Gly<br>                405              410              415 | 1248 |
| gac ggc atc cat cgc gtc acc ctc gac cag gtc atc gac acc atg cgc<br>Asp Gly Ile His Arg Val Thr Leu Asp Gln Val Ile Asp Thr Met Arg<br>         420               425              430 | 1296 |
| gcc acc ggc gcg gac atg cac acc aag tac aag gaa acc tcg gcc ggc<br>Ala Thr Gly Ala Asp Met His Thr Lys Tyr Lys Glu Thr Ser Ala Gly<br>435                440              445 | 1344 |
| ggg ctc gcc atc aac gtc gca gtc aac atc gtc gag tgt tga<br>Gly Leu Ala Ile Asn Val Ala Val Asn Ile Val Glu Cys | 1386 |

```
          450            455            460

<210> SEQ ID NO 6
<211> LENGTH: 461
<212> TYPE: PRT
<213> ORGANISM: Mycobacterium tuberculosis
<220> FEATURE:
<221> NAME/KEY:
<222> LOCATION:
<223> OTHER INFORMATION: Sequence is identical to SwissProt entry SP:
      SDHL_MYCTU Sequence is identical to GenBank entries GP:
      AE006919_13 and GP:MTV030_11

<400> SEQUENCE: 6

Met Thr Ile Ser Val Phe Asp Leu Phe Thr Ile Gly Ile Gly Pro Ser
1               5                   10                  15

Ser Ser His Thr Val Gly Pro Met Arg Ala Ala Asn Gln Phe Val Val
                20                  25                  30

Ala Leu Arg Arg Arg Gly His Leu Asp Asp Leu Glu Ala Met Arg Val
            35                  40                  45

Asp Leu Phe Gly Ser Leu Ala Ala Thr Gly Ala Gly His Gly Thr Met
    50                  55                  60

Ser Ala Ile Leu Leu Gly Leu Glu Gly Cys Gln Pro Glu Thr Ile Thr
65                  70                  75                  80

Thr Glu His Lys Glu Arg Arg Leu Ala Glu Ile Ala Ala Ser Gly Val
                85                  90                  95

Thr Arg Ile Gly Gly Val Ile Pro Val Pro Leu Thr Glu Arg Asp Ile
            100                 105                 110

Asp Leu His Pro Asp Ile Val Leu Pro Thr His Pro Asn Gly Met Thr
    115                 120                 125

Phe Thr Ala Ala Gly Pro His Gly Arg Val Leu Ala Thr Glu Thr Tyr
130                 135                 140

Phe Ser Val Gly Gly Gly Phe Ile Val Thr Glu Gln Thr Ser Gly Asn
145                 150                 155                 160

Ser Gly Gln His Pro Cys Ser Val Ala Leu Pro Tyr Val Ser Ala Gln
                165                 170                 175

Glu Leu Leu Asp Ile Cys Asp Arg Leu Asp Val Ser Ile Ser Glu Ala
            180                 185                 190

Ala Leu Arg Asn Glu Thr Cys Cys Arg Thr Glu Asn Glu Val Arg Ala
    195                 200                 205

Ala Leu Leu His Leu Arg Asp Val Met Val Glu Cys Glu Gln Arg Ser
210                 215                 220

Ile Ala Arg Glu Gly Leu Leu Pro Gly Gly Leu Arg Val Arg Arg Arg
225                 230                 235                 240

Ala Lys Val Trp Tyr Asp Arg Leu Asn Ala Glu Asp Pro Thr Arg Lys
                245                 250                 255

Pro Glu Phe Ala Glu Asp Trp Val Asn Leu Val Ala Leu Ala Val Asn
            260                 265                 270

Glu Glu Asn Ala Ser Gly Gly Arg Val Val Thr Ala Pro Thr Asn Gly
    275                 280                 285

Ala Ala Gly Ile Val Pro Ala Val Leu His Tyr Ala Ile His Tyr Thr
290                 295                 300

Ser Ala Gly Ala Gly Asp Pro Asp Asp Val Thr Val Arg Phe Leu Leu
305                 310                 315                 320

Thr Ala Gly Ala Ile Gly Ser Leu Phe Lys Glu Arg Ala Ser Ile Ser
                325                 330                 335
```

-continued

```
Gly Ala Glu Val Gly Cys Gln Gly Glu Val Gly Ser Ala Ala Ala Met
                340                 345                 350

Ala Ala Ala Gly Leu Ala Glu Ile Leu Gly Gly Thr Pro Arg Gln Val
            355                 360                 365

Glu Asn Ala Ala Glu Ile Ala Met Glu His Ser Leu Gly Leu Thr Cys
        370                 375                 380

Asp Pro Ile Ala Gly Leu Val Gln Ile Pro Cys Ile Glu Arg Asn Ala
385                 390                 395                 400

Ile Ser Ala Gly Lys Ala Ile Asn Ala Ala Arg Met Ala Leu Arg Gly
                405                 410                 415

Asp Gly Ile His Arg Val Thr Leu Asp Gln Val Ile Asp Thr Met Arg
            420                 425                 430

Ala Thr Gly Ala Asp Met His Thr Lys Tyr Lys Glu Thr Ser Ala Gly
        435                 440                 445

Gly Leu Ala Ile Asn Val Ala Val Asn Ile Val Glu Cys
    450                 455                 460

<210> SEQ ID NO 7
<211> LENGTH: 1437
<212> TYPE: DNA
<213> ORGANISM: Mycobacterium tuberculosis
<220> FEATURE:
<221> NAME/KEY: CDS
<222> LOCATION: (1)..(1437)
<223> OTHER INFORMATION: Sequence is identical to GenBank entry GB:
      MTU87280 [U87280]Sequence is identical to nucleotides 163-1599
      of GenBank entry GB:MTCY427 [Z70692] Sequence is identical to
      nucleotides 93-1529 of GenBank entry GB:AE007073

<400> SEQUENCE: 7 gtg acg gaa aag acg ccc gac gac gtc ttc aaa ctt gcc aag gac gag      48
Met Thr Glu Lys Thr Pro Asp Asp Val Phe Lys Leu Ala Lys Asp Glu
1               5                   10                  15 aag gtc gaa tat gtc gac gtc cgg ttc tgt gac ctg cct ggc atc atg      96
Lys Val Glu Tyr Val Asp Val Arg Phe Cys Asp Leu Pro Gly Ile Met
                20                  25                  30 cag cac ttc acg att ccg gct tcg gcc ttt gac aag agc gtg ttt gac     144
Gln His Phe Thr Ile Pro Ala Ser Ala Phe Asp Lys Ser Val Phe Asp
            35                  40                  45 gac ggc ttg gcc ttt gac ggc tcg tcg att cgc ggg ttc cag tcg atc     192
Asp Gly Leu Ala Phe Asp Gly Ser Ser Ile Arg Gly Phe Gln Ser Ile
        50                  55                  60 cac gaa tcc gac atg ttg ctt ctt ccc gat ccc gag acg gcg cgc atc     240
His Glu Ser Asp Met Leu Leu Leu Pro Asp Pro Glu Thr Ala Arg Ile
65                  70                  75                  80 gac ccg ttc cgc gcg gcc aag acg ctg aat atc aac ttc ttt gtg cac     288
Asp Pro Phe Arg Ala Ala Lys Thr Leu Asn Ile Asn Phe Phe Val His
                85                  90                  95 gac ccg ttc acc ctg gag ccg tac tcc cgc gac ccg cgc aac atc gcc     336
Asp Pro Phe Thr Leu Glu Pro Tyr Ser Arg Asp Pro Arg Asn Ile Ala
                100                 105                 110 cgc aag gcc gag aac tac ctg atc agc act ggc atc gcc gac acc gca     384
Arg Lys Ala Glu Asn Tyr Leu Ile Ser Thr Gly Ile Ala Asp Thr Ala
            115                 120                 125 tac ttc ggc gcc gag gcc gag ttc tac att ttc gat tcg gtg agc ttc     432
Tyr Phe Gly Ala Glu Ala Glu Phe Tyr Ile Phe Asp Ser Val Ser Phe
        130                 135                 140 gac tcg cgc gcc aac ggc tcc ttc tac gag gtg gac gcc atc tcg ggg     480
Asp Ser Arg Ala Asn Gly Ser Phe Tyr Glu Val Asp Ala Ile Ser Gly
145                 150                 155                 160
```

```
tgg tgg aac acc ggc gcg gcg acc gag gcc gac ggt agt ccc aac cgg      528
Trp Trp Asn Thr Gly Ala Ala Thr Glu Ala Asp Gly Ser Pro Asn Arg
            165                 170                 175 ggc tac aag gtc cgc cac aag ggc ggg tat ttc cca gtg gcc ccc aac      576
Gly Tyr Lys Val Arg His Lys Gly Gly Tyr Phe Pro Val Ala Pro Asn
        180                 185                 190 gac caa tac gtc gac ctg cgc gac aag atg ctg acc aac ctg atc aac      624
Asp Gln Tyr Val Asp Leu Arg Asp Lys Met Leu Thr Asn Leu Ile Asn
    195                 200                 205 tcc ggc ttc atc ctg gag aag ggc cac cac gag gtg ggc agc ggc gga      672
Ser Gly Phe Ile Leu Glu Lys Gly His His Glu Val Gly Ser Gly Gly
210                 215                 220 cag gcc gag atc aac tac cag ttc aat tcg ctg ctg cac gcc gcc gac      720
Gln Ala Glu Ile Asn Tyr Gln Phe Asn Ser Leu Leu His Ala Ala Asp
225                 230                 235                 240 gac atg cag ttg tac aag tac atc atc aag aac acc gcc tgg cag aac      768
Asp Met Gln Leu Tyr Lys Tyr Ile Ile Lys Asn Thr Ala Trp Gln Asn
            245                 250                 255 ggc aaa acg gtc acg ttc atg ccc aag ccg ctg ttc ggc gac aac ggg      816
Gly Lys Thr Val Thr Phe Met Pro Lys Pro Leu Phe Gly Asp Asn Gly
        260                 265                 270 tcc ggc atg cac tgt cat cag tcg ctg tgg aag gac ggg gcc ccg ctg      864
Ser Gly Met His Cys His Gln Ser Leu Trp Lys Asp Gly Ala Pro Leu
    275                 280                 285 atg tac gac gag acg ggt tat gcc ggt ctg tcg gac acg gcc cgt cat      912
Met Tyr Asp Glu Thr Gly Tyr Ala Gly Leu Ser Asp Thr Ala Arg His
290                 295                 300 tac atc ggc ggc ctg tta cac cac gcg ccg tcg ctg ctg gcc ttc acc      960
Tyr Ile Gly Gly Leu Leu His His Ala Pro Ser Leu Leu Ala Phe Thr
305                 310                 315                 320 aac ccg acg gtg aac tcc tac aag cgg ctg gtt ccc ggt tac gag gcc     1008
Asn Pro Thr Val Asn Ser Tyr Lys Arg Leu Val Pro Gly Tyr Glu Ala
            325                 330                 335 ccg atc aac ctg gtc tat agc cag cgc aac cgg tcg gca tgc gtg cgc     1056
Pro Ile Asn Leu Val Tyr Ser Gln Arg Asn Arg Ser Ala Cys Val Arg
        340                 345                 350 atc ccg atc acc ggc agc aac ccg aag gcc aag cgg ctg gag ttc cga     1104
Ile Pro Ile Thr Gly Ser Asn Pro Lys Ala Lys Arg Leu Glu Phe Arg
    355                 360                 365 agc ccc gac tcg tcg ggc aac ccg tat ctg gcg ttc tcg gcc atg ctg     1152
Ser Pro Asp Ser Ser Gly Asn Pro Tyr Leu Ala Phe Ser Ala Met Leu
370                 375                 380 atg gca ggc ctg gac ggt atc aag aac aag atc gag ccg cag gcg ccc     1200
Met Ala Gly Leu Asp Gly Ile Lys Asn Lys Ile Glu Pro Gln Ala Pro
385                 390                 395                 400 gtc gac aag gat ctc tac gag ctg ccg ccg gaa gag gcc gcg agt atc     1248
Val Asp Lys Asp Leu Tyr Glu Leu Pro Pro Glu Glu Ala Ala Ser Ile
            405                 410                 415 ccg cag act ccg acc cag ctg tca gat gtg atc gac cgt ctc gag gcc     1296
Pro Gln Thr Pro Thr Gln Leu Ser Asp Val Ile Asp Arg Leu Glu Ala
        420                 425                 430 gac cac gaa tac ctc acc gaa gga ggg gtg ttc aca aac gac ctg atc     1344
Asp His Glu Tyr Leu Thr Glu Gly Gly Val Phe Thr Asn Asp Leu Ile
    435                 440                 445 gag acg tgg atc agt ttc aag cgc gaa aac gag atc gag ccg gtc aac     1392
Glu Thr Trp Ile Ser Phe Lys Arg Glu Asn Glu Ile Glu Pro Val Asn
450                 455                 460 atc cgg ccg cat ccc tac gaa ttc gcg ctg tac tac gac gtt taa         1437
Ile Arg Pro His Pro Tyr Glu Phe Ala Leu Tyr Tyr Asp Val
465                 470                 475
```

<210> SEQ ID NO 8
<211> LENGTH: 478
<212> TYPE: PRT
<213> ORGANISM: Mycobacterium tuberculosis
<220> FEATURE:
<221> NAME/KEY:
<222> LOCATION:
<223> OTHER INFORMATION: Sequence is identical to SwissProt entry SP:
      GLN1_MYCTU Sequence is identical to PIR entry PIR:H70775
      Sequence is identical to PRF entry PRF:2323405A

<400> SEQUENCE: 8

```
Met Thr Glu Lys Thr Pro Asp Asp Val Phe Lys Leu Ala Lys Asp Glu
 1               5                  10                  15

Lys Val Glu Tyr Val Asp Val Arg Phe Cys Asp Leu Pro Gly Ile Met
            20                  25                  30

Gln His Phe Thr Ile Pro Ala Ser Ala Phe Asp Lys Ser Val Phe Asp
        35                  40                  45

Asp Gly Leu Ala Phe Asp Gly Ser Ser Ile Arg Gly Phe Gln Ser Ile
    50                  55                  60

His Glu Ser Asp Met Leu Leu Leu Pro Asp Pro Glu Thr Ala Arg Ile
65                  70                  75                  80

Asp Pro Phe Arg Ala Ala Lys Thr Leu Asn Ile Asn Phe Phe Val His
                85                  90                  95

Asp Pro Phe Thr Leu Glu Pro Tyr Ser Arg Asp Pro Arg Asn Ile Ala
            100                 105                 110

Arg Lys Ala Glu Asn Tyr Leu Ile Ser Thr Gly Ile Ala Asp Thr Ala
        115                 120                 125

Tyr Phe Gly Ala Glu Ala Glu Phe Tyr Ile Phe Asp Ser Val Ser Phe
    130                 135                 140

Asp Ser Arg Ala Asn Gly Ser Phe Tyr Glu Val Asp Ala Ile Ser Gly
145                 150                 155                 160

Trp Trp Asn Thr Gly Ala Ala Thr Glu Ala Asp Gly Ser Pro Asn Arg
                165                 170                 175

Gly Tyr Lys Val Arg His Lys Gly Gly Tyr Phe Pro Val Ala Pro Asn
            180                 185                 190

Asp Gln Tyr Val Asp Leu Arg Asp Lys Met Leu Thr Asn Leu Ile Asn
        195                 200                 205

Ser Gly Phe Ile Leu Glu Lys Gly His His Glu Val Gly Ser Gly Gly
    210                 215                 220

Gln Ala Glu Ile Asn Tyr Gln Phe Asn Ser Leu Leu His Ala Ala Asp
225                 230                 235                 240

Asp Met Gln Leu Tyr Lys Tyr Ile Ile Lys Asn Thr Ala Trp Gln Asn
                245                 250                 255

Gly Lys Thr Val Thr Phe Met Pro Lys Pro Leu Phe Gly Asp Asn Gly
            260                 265                 270

Ser Gly Met His Cys His Gln Ser Leu Trp Lys Asp Gly Ala Pro Leu
        275                 280                 285

Met Tyr Asp Glu Thr Gly Tyr Ala Gly Leu Ser Asp Thr Ala Arg His
    290                 295                 300

Tyr Ile Gly Gly Leu Leu His His Ala Pro Ser Leu Leu Ala Phe Thr
305                 310                 315                 320

Asn Pro Thr Val Asn Ser Tyr Lys Arg Leu Val Pro Gly Tyr Glu Ala
                325                 330                 335

Pro Ile Asn Leu Val Tyr Ser Gln Arg Asn Arg Ser Ala Cys Val Arg
```

-continued

```
                340                 345                 350
Ile Pro Ile Thr Gly Ser Asn Pro Lys Ala Lys Arg Leu Glu Phe Arg
            355                 360                 365

Ser Pro Asp Ser Ser Gly Asn Pro Tyr Leu Ala Phe Ser Ala Met Leu
        370                 375                 380

Met Ala Gly Leu Asp Gly Ile Lys Asn Lys Ile Glu Pro Gln Ala Pro
385                 390                 395                 400

Val Asp Lys Asp Leu Tyr Glu Leu Pro Pro Glu Ala Ala Ser Ile
                405                 410                 415

Pro Gln Thr Pro Thr Gln Leu Ser Asp Val Ile Asp Arg Leu Glu Ala
            420                 425                 430

Asp His Glu Tyr Leu Thr Glu Gly Gly Val Phe Thr Asn Asp Leu Ile
        435                 440                 445

Glu Thr Trp Ile Ser Phe Lys Arg Glu Asn Glu Ile Glu Pro Val Asn
    450                 455                 460

Ile Arg Pro His Pro Tyr Glu Phe Ala Leu Tyr Tyr Asp Val
465                 470                 475
```

<210> SEQ ID NO 9
<211> LENGTH: 1341
<212> TYPE: DNA
<213> ORGANISM: Mycobacterium tuberculosis
<220> FEATURE:
<221> NAME/KEY: CDS
<222> LOCATION: (1)..(1341)
<223> OTHER INFORMATION: Sequence is identical to complement of
      nucleotides 4950-6290of GenBank entry GB:MTCY427 [Z70692]
      Sequence is identical to complement of nucleotides 4880-6220
      of GenBank entry GB:AE007073

<400> SEQUENCE: 9

```
atg gac cga cag aag gaa ttc gtt ctt cgt acc ctg gaa gaa cgc gac      48
Met Asp Arg Gln Lys Glu Phe Val Leu Arg Thr Leu Glu Glu Arg Asp
1               5                   10                  15 atc cgc ttc gtc cgg ctg tgg ttc aca gac gtg ctc ggt ttc ctc aag      96
Ile Arg Phe Val Arg Leu Trp Phe Thr Asp Val Leu Gly Phe Leu Lys
            20                  25                  30 tcg gtc gcc atc gcc cca gcc gaa ctc gag ggc gcc ttc gag gaa ggc     144
Ser Val Ala Ile Ala Pro Ala Glu Leu Glu Gly Ala Phe Glu Glu Gly
        35                  40                  45 atc ggc ttc gac gga tcc tcg atc gag ggc ttt gcg cgg gtc tcg gaa     192
Ile Gly Phe Asp Gly Ser Ser Ile Glu Gly Phe Ala Arg Val Ser Glu
    50                  55                  60 tcc gat acg gtg gcg cac ccg gac ccg tcg acc ttc cag gtg ctg ccc     240
Ser Asp Thr Val Ala His Pro Asp Pro Ser Thr Phe Gln Val Leu Pro
65                  70                  75                  80 tgg gcc acc agt tcc ggc cac cac cac tca gcg cgg atg ttt tgc gac     288
Trp Ala Thr Ser Ser Gly His His His Ser Ala Arg Met Phe Cys Asp
                85                  90                  95 atc acc atg ccg gac ggc tcg ccg tcg tgg gcg gac ccg cgg cac gtg     336
Ile Thr Met Pro Asp Gly Ser Pro Ser Trp Ala Asp Pro Arg His Val
            100                 105                 110 ttg cgg cgg cag ctg acg aag gcc ggc gaa ctc ggc ttc tcc tgc tac     384
Leu Arg Arg Gln Leu Thr Lys Ala Gly Glu Leu Gly Phe Ser Cys Tyr
        115                 120                 125 gtg cat ccc gaa atc gag ttc ttc ctg ctc aag ccc gga ccc gag gac     432
Val His Pro Glu Ile Glu Phe Phe Leu Leu Lys Pro Gly Pro Glu Asp
    130                 135                 140 ggg tcg gtg ccc gtc ccg gtc gac aac gcc ggc tat ttc gac caa gcg     480
Gly Ser Val Pro Val Pro Val Asp Asn Ala Gly Tyr Phe Asp Gln Ala
```

```
                145                 150                 155                 160
gtg cac gac tcc gcc ttg aac ttt cgc cgc cac gcg atc gat gcc ctg         528
Val His Asp Ser Ala Leu Asn Phe Arg Arg His Ala Ile Asp Ala Leu
                165                 170                 175 gaa ttc atg ggc atc tcg gtg gag ttc agc cat cac gaa ggc gca ccc         576
Glu Phe Met Gly Ile Ser Val Glu Phe Ser His His Glu Gly Ala Pro
            180                 185                 190 ggc cag cag gag atc gac ctg cgg ttt gcc gac gct ctg tcg atg gct         624
Gly Gln Gln Glu Ile Asp Leu Arg Phe Ala Asp Ala Leu Ser Met Ala
        195                 200                 205 gac aac gtg atg acc ttc cgc tac gtc atc aaa gaa gtc gcg ctg gaa         672
Asp Asn Val Met Thr Phe Arg Tyr Val Ile Lys Glu Val Ala Leu Glu
    210                 215                 220 gag ggc gcc cgg gcg tcg ttc atg ccc aag cca ttc ggc cag cac ccg         720
Glu Gly Ala Arg Ala Ser Phe Met Pro Lys Pro Phe Gly Gln His Pro
225                 230                 235                 240 ggc tcg gcg atg cac acc cac atg agc ctg ttc gag ggt gat gtc aac         768
Gly Ser Ala Met His Thr His Met Ser Leu Phe Glu Gly Asp Val Asn
                245                 250                 255 gcg ttc cac agc gct gat gat ccg ctg cag ctg tcg gaa gtg ggt aaa         816
Ala Phe His Ser Ala Asp Asp Pro Leu Gln Leu Ser Glu Val Gly Lys
            260                 265                 270 tcg ttc atc gcc ggg atc ctg gag cac gct tgc gag atc agc gcg gtc         864
Ser Phe Ile Ala Gly Ile Leu Glu His Ala Cys Glu Ile Ser Ala Val
        275                 280                 285 aca aat cag tgg gtc aac tct tac aag cgg ctg gtg cag ggc ggc gaa         912
Thr Asn Gln Trp Val Asn Ser Tyr Lys Arg Leu Val Gln Gly Gly Glu
    290                 295                 300 gcg ccc acg gcc gcg tcg tgg ggg gcc gcc aac cga tcc gcc cta gtg         960
Ala Pro Thr Ala Ala Ser Trp Gly Ala Ala Asn Arg Ser Ala Leu Val
305                 310                 315                 320 cgg gtg ccg atg tac acg ccg cac aag acc tcg tcg cgg cgg gtc gaa        1008
Arg Val Pro Met Tyr Thr Pro His Lys Thr Ser Ser Arg Arg Val Glu
                325                 330                 335 gta cgc agc cct gat tcg gcg tgc aat ccc tat ctg aca ttc gcc gtg        1056
Val Arg Ser Pro Asp Ser Ala Cys Asn Pro Tyr Leu Thr Phe Ala Val
            340                 345                 350 ctg ctg gcc gcg gga ttg cgg ggt gta gag aag ggt tac gtg ctg ggc        1104
Leu Leu Ala Ala Gly Leu Arg Gly Val Glu Lys Gly Tyr Val Leu Gly
        355                 360                 365 ccg cag gcc gag gac aac gta tgg gac ctc aca ccc gag gaa cgc cga        1152
Pro Gln Ala Glu Asp Asn Val Trp Asp Leu Thr Pro Glu Glu Arg Arg
    370                 375                 380 gcg atg ggg tac cga gaa ttg ccg tcc agt ttg gat agt gcg ctg cgc        1200
Ala Met Gly Tyr Arg Glu Leu Pro Ser Ser Leu Asp Ser Ala Leu Arg
385                 390                 395                 400 gcc atg gag gcc tcc gaa ctc gtc gcg gag gcc ttg ggg gag cac gtt        1248
Ala Met Glu Ala Ser Glu Leu Val Ala Glu Ala Leu Gly Glu His Val
                405                 410                 415 ttt gac ttt ttc ttg cgc aac aag cgc acg gag tgg gcg aac tac cgc        1296
Phe Asp Phe Phe Leu Arg Asn Lys Arg Thr Glu Trp Ala Asn Tyr Arg
            420                 425                 430 agc cac gtc acg cca tac gag ctg cgc acc tac ctg tcg ctg tag            1341
Ser His Val Thr Pro Tyr Glu Leu Arg Thr Tyr Leu Ser Leu
        435                 440                 445

<210> SEQ ID NO 10
<211> LENGTH: 446
<212> TYPE: PRT
<213> ORGANISM: Mycobacterium tuberculosis
```

```
<220> FEATURE:
<221> NAME/KEY:
<222> LOCATION:
<223> OTHER INFORMATION: Sequence is identical to SwissProt entry SP:
      GLN2_MYCTU Sequence is identical to PIR entry PIR:B70776

<400> SEQUENCE: 10

Met Asp Arg Gln Lys Glu Phe Val Leu Arg Thr Leu Glu Glu Arg Asp
1               5                   10                  15

Ile Arg Phe Val Arg Leu Trp Phe Thr Asp Val Leu Gly Phe Leu Lys
            20                  25                  30

Ser Val Ala Ile Ala Pro Ala Glu Leu Glu Gly Ala Phe Glu Glu Gly
        35                  40                  45

Ile Gly Phe Asp Gly Ser Ser Ile Glu Gly Phe Ala Arg Val Ser Glu
    50                  55                  60

Ser Asp Thr Val Ala His Pro Asp Pro Ser Thr Phe Gln Val Leu Pro
65                  70                  75                  80

Trp Ala Thr Ser Ser Gly His His Ser Ala Arg Met Phe Cys Asp
                85                  90                  95

Ile Thr Met Pro Asp Gly Ser Pro Ser Trp Ala Asp Pro Arg His Val
            100                 105                 110

Leu Arg Arg Gln Leu Thr Lys Ala Gly Glu Leu Gly Phe Ser Cys Tyr
        115                 120                 125

Val His Pro Glu Ile Glu Phe Phe Leu Leu Lys Pro Gly Pro Glu Asp
    130                 135                 140

Gly Ser Val Pro Val Pro Val Asp Asn Ala Gly Tyr Phe Asp Gln Ala
145                 150                 155                 160

Val His Asp Ser Ala Leu Asn Phe Arg Arg His Ala Ile Asp Ala Leu
                165                 170                 175

Glu Phe Met Gly Ile Ser Val Glu Phe Ser His His Glu Gly Ala Pro
            180                 185                 190

Gly Gln Gln Glu Ile Asp Leu Arg Phe Ala Asp Ala Leu Ser Met Ala
        195                 200                 205

Asp Asn Val Met Thr Phe Arg Tyr Val Ile Lys Glu Val Ala Leu Glu
    210                 215                 220

Glu Gly Ala Arg Ala Ser Phe Met Pro Lys Pro Phe Gly Gln His Pro
225                 230                 235                 240

Gly Ser Ala Met His Thr His Met Ser Leu Phe Glu Gly Asp Val Asn
                245                 250                 255

Ala Phe His Ser Ala Asp Asp Pro Leu Gln Leu Ser Glu Val Gly Lys
            260                 265                 270

Ser Phe Ile Ala Gly Ile Leu Glu His Ala Cys Glu Ile Ser Ala Val
        275                 280                 285

Thr Asn Gln Trp Val Asn Ser Tyr Lys Arg Leu Val Gln Gly Gly Glu
    290                 295                 300

Ala Pro Thr Ala Ala Ser Trp Gly Ala Ala Asn Arg Ser Ala Leu Val
305                 310                 315                 320

Arg Val Pro Met Tyr Thr Pro His Lys Thr Ser Ser Arg Val Glu
                325                 330                 335

Val Arg Ser Pro Asp Ser Ala Cys Asn Pro Tyr Leu Thr Phe Ala Val
            340                 345                 350

Leu Leu Ala Ala Gly Leu Arg Gly Val Glu Lys Gly Tyr Val Leu Gly
        355                 360                 365

Pro Gln Ala Glu Asp Asn Val Trp Asp Leu Thr Pro Glu Glu Arg Arg
    370                 375                 380
```

```
Ala Met Gly Tyr Arg Glu Leu Pro Ser Ser Leu Asp Ser Ala Leu Arg
385                 390                 395                 400

Ala Met Glu Ala Ser Glu Leu Val Ala Glu Ala Leu Gly Glu His Val
                405                 410                 415

Phe Asp Phe Phe Leu Arg Asn Lys Arg Thr Glu Trp Ala Asn Tyr Arg
                420                 425                 430

Ser His Val Thr Pro Tyr Glu Leu Arg Thr Tyr Leu Ser Leu
                435                 440                 445

<210> SEQ ID NO 11
<211> LENGTH: 1353
<212> TYPE: DNA
<213> ORGANISM: Mycobacterium tuberculosis
<220> FEATURE:
<221> NAME/KEY: CDS
<222> LOCATION: (1)..(1353)
<223> OTHER INFORMATION: Sequence is identical to nucleotides 4871-6223
      of GenBank entry GB:MTCY180 [Z97193]
      Sequence is identical to nucleotides 7308-8660
      of GenBank entry GB:AE007049

<400> SEQUENCE: 11 atg aca gcc aca ccg ctt gcc gcg gcc gcg atc gcc caa ttg gag gca    48
Met Thr Ala Thr Pro Leu Ala Ala Ala Ala Ile Ala Gln Leu Glu Ala
1               5                   10                  15 gag ggc gtc gac acc gtc atc ggc acc gtc gtg aac ccc gcc gga ctc    96
Glu Gly Val Asp Thr Val Ile Gly Thr Val Val Asn Pro Ala Gly Leu
            20                  25                  30 acc cag gcc aag acc gtg ccg ata cgc cgg acc aac aca ttc gcc aat    144
Thr Gln Ala Lys Thr Val Pro Ile Arg Arg Thr Asn Thr Phe Ala Asn
        35                  40                  45 cct ggc ctc ggc gcc agt ccg gtg tgg cat acc ttc tgt atc gac caa    192
Pro Gly Leu Gly Ala Ser Pro Val Trp His Thr Phe Cys Ile Asp Gln
    50                  55                  60 tgc agt att gca ttc acc gca gac atc agt gtg gtc ggc gat caa cgt    240
Cys Ser Ile Ala Phe Thr Ala Asp Ile Ser Val Val Gly Asp Gln Arg
65                  70                  75                  80 ctc cgc atc gat ctg tcc gcc ttg cgc atc atc ggc gac ggg ttg gcg    288
Leu Arg Ile Asp Leu Ser Ala Leu Arg Ile Ile Gly Asp Gly Leu Ala
                85                  90                  95 tgg gcg ccc gcc ggg ttc ttc gag cag gac ggc aca ccg gtc ccc gcc    336
Trp Ala Pro Ala Gly Phe Phe Glu Gln Asp Gly Thr Pro Val Pro Ala
            100                 105                 110 tgc agc cga gga aca ctg agc cgg atc gag gcc gcg ctt gct gat gcc    384
Cys Ser Arg Gly Thr Leu Ser Arg Ile Glu Ala Ala Leu Ala Asp Ala
        115                 120                 125 ggc atc gac gcg gta atc ggc cac gaa gtc gaa ttc ctc ttg gtc gac    432
Gly Ile Asp Ala Val Ile Gly His Glu Val Glu Phe Leu Leu Val Asp
    130                 135                 140 gcg gac ggc cag cgg ctg cct tcg acg ctg tgg gcg cag tac ggt gtc    480
Ala Asp Gly Gln Arg Leu Pro Ser Thr Leu Trp Ala Gln Tyr Gly Val
145                 150                 155                 160 gcc ggg gtg ctc gag cac gag gcg ttc gtc cgc gat gtc aac gcc gcg    528
Ala Gly Val Leu Glu His Glu Ala Phe Val Arg Asp Val Asn Ala Ala
                165                 170                 175 gca acg gca gca ggc atc gct atc gag cag ttc cat ccc gaa tac ggt    576
Ala Thr Ala Ala Gly Ile Ala Ile Glu Gln Phe His Pro Glu Tyr Gly
            180                 185                 190 gcc aac caa ttc gag atc tcg tta gcg ccg cag ccg ccg gtc gcg gcc    624
Ala Asn Gln Phe Glu Ile Ser Leu Ala Pro Gln Pro Pro Val Ala Ala
        195                 200                 205
```

-continued

```
gcc gat cag ctg gtg ctg acc cgc ctc atc atc ggc cgt acc gcc cgc       672
Ala Asp Gln Leu Val Leu Thr Arg Leu Ile Ile Gly Arg Thr Ala Arg
    210                 215                 220 cgg cac ggg tta cgc gtg agc cta tcg cca gcg ccc ttc gcc gga agt       720
Arg His Gly Leu Arg Val Ser Leu Ser Pro Ala Pro Phe Ala Gly Ser
225                 230                 235                 240 atc gga tcc ggt gcc cac caa cac ttc tcg ctg act atg tcg gaa ggg       768
Ile Gly Ser Gly Ala His Gln His Phe Ser Leu Thr Met Ser Glu Gly
                245                 250                 255 atg ctg ttc tcc ggt ggg act gga gca gct ggc atg acc tcg gcc ggg       816
Met Leu Phe Ser Gly Gly Thr Gly Ala Ala Gly Met Thr Ser Ala Gly
            260                 265                 270 gag gcc gcg gtg gca gga gtg ctt cgc gga cta ccg gac gcc caa ggc       864
Glu Ala Ala Val Ala Gly Val Leu Arg Gly Leu Pro Asp Ala Gln Gly
        275                 280                 285 atc ctg tgc gga tcg atc gtg tcc ggt ctg cga atg cga ccc ggt aac       912
Ile Leu Cys Gly Ser Ile Val Ser Gly Leu Arg Met Arg Pro Gly Asn
    290                 295                 300 tgg gcc gga atc tat gca tgc tgg ggt acc gaa aac cgg gaa gcg gcg       960
Trp Ala Gly Ile Tyr Ala Cys Trp Gly Thr Glu Asn Arg Glu Ala Ala
305                 310                 315                 320 gtg cga ttc gtc aag ggc ggg gct ggc agc gcg tac ggc ggg aac gtg      1008
Val Arg Phe Val Lys Gly Gly Ala Gly Ser Ala Tyr Gly Gly Asn Val
                325                 330                 335 gag gtg aag gtc gtc gac ccg tcg gcc aac ccg tat ctc gcg tcg gcg      1056
Glu Val Lys Val Val Asp Pro Ser Ala Asn Pro Tyr Leu Ala Ser Ala
            340                 345                 350 gcg atc ctc gga ctg gca ctc gac ggc atg aag acc aag gcg gtg ttg      1104
Ala Ile Leu Gly Leu Ala Leu Asp Gly Met Lys Thr Lys Ala Val Leu
        355                 360                 365 ccg tcg gaa acg acc gta gac ccg aca cag ctg tct gac gtg gat cgt      1152
Pro Ser Glu Thr Thr Val Asp Pro Thr Gln Leu Ser Asp Val Asp Arg
    370                 375                 380 gac cgt gcc ggc att ctg cga ctt gct gcc gat cag gcg gat gca att      1200
Asp Arg Ala Gly Ile Leu Arg Leu Ala Ala Asp Gln Ala Asp Ala Ile
385                 390                 395                 400 gct gta ctg gat agt tcg aaa ctg ctt cgg tgc atc ctt ggc gat ccc      1248
Ala Val Leu Asp Ser Ser Lys Leu Leu Arg Cys Ile Leu Gly Asp Pro
                405                 410                 415 gtg gta gat gcc gtg gtc gcg gta cgc cag tta gag cat gag cgc tac      1296
Val Val Asp Ala Val Val Ala Val Arg Gln Leu Glu His Glu Arg Tyr
            420                 425                 430 ggt gac ctc gat cct gcg cag ctg gcc gac aag ttc cgg atg gct tgg      1344
Gly Asp Leu Asp Pro Ala Gln Leu Ala Asp Lys Phe Arg Met Ala Trp
        435                 440                 445 agt gtg taa                                                          1353
Ser Val
    450
```

<210> SEQ ID NO 12
<211> LENGTH: 450
<212> TYPE: PRT
<213> ORGANISM: Mycobacterium tuberculosis
<220> FEATURE:
<221> NAME/KEY:
<222> LOCATION:
<223> OTHER INFORMATION: Sequence is identical to PIR entry PIR:C70515

<400> SEQUENCE: 12

```
Met Thr Ala Thr Pro Leu Ala Ala Ala Ile Ala Gln Leu Glu Ala
1               5                   10                  15
```

```
Glu Gly Val Asp Thr Val Ile Gly Thr Val Asn Pro Ala Gly Leu
            20                  25                  30

Thr Gln Ala Lys Thr Val Pro Ile Arg Arg Thr Asn Thr Phe Ala Asn
            35                  40                  45

Pro Gly Leu Gly Ala Ser Pro Val Trp His Thr Phe Cys Ile Asp Gln
 50              55                  60

Cys Ser Ile Ala Phe Thr Ala Asp Ile Ser Val Gly Asp Gln Arg
 65              70                  75                  80

Leu Arg Ile Asp Leu Ser Ala Leu Arg Ile Ile Gly Asp Gly Leu Ala
                85                  90                  95

Trp Ala Pro Ala Gly Phe Phe Glu Gln Asp Gly Thr Pro Val Pro Ala
                100                 105                 110

Cys Ser Arg Gly Thr Leu Ser Arg Ile Glu Ala Ala Leu Ala Asp Ala
                115                 120                 125

Gly Ile Asp Ala Val Ile Gly His Glu Val Glu Phe Leu Leu Val Asp
            130                 135                 140

Ala Asp Gly Gln Arg Leu Pro Ser Thr Leu Trp Ala Gln Tyr Gly Val
145                 150                 155                 160

Ala Gly Val Leu Glu His Glu Ala Phe Val Arg Asp Val Asn Ala Ala
                165                 170                 175

Ala Thr Ala Ala Gly Ile Ala Ile Glu Gln Phe His Pro Glu Tyr Gly
                180                 185                 190

Ala Asn Gln Phe Glu Ile Ser Leu Ala Pro Gln Pro Val Ala Ala
                195                 200                 205

Ala Asp Gln Leu Val Leu Thr Arg Leu Ile Ile Gly Arg Thr Ala Arg
210                 215                 220

Arg His Gly Leu Arg Val Ser Leu Ser Pro Ala Pro Phe Ala Gly Ser
225                 230                 235                 240

Ile Gly Ser Gly Ala His Gln His Phe Ser Leu Thr Met Ser Glu Gly
                245                 250                 255

Met Leu Phe Ser Gly Gly Thr Gly Ala Ala Gly Met Thr Ser Ala Gly
                260                 265                 270

Glu Ala Ala Val Ala Gly Val Leu Arg Gly Leu Pro Asp Ala Gln Gly
                275                 280                 285

Ile Leu Cys Gly Ser Ile Val Ser Gly Leu Arg Met Arg Pro Gly Asn
            290                 295                 300

Trp Ala Gly Ile Tyr Ala Cys Trp Gly Thr Glu Asn Arg Glu Ala Ala
305                 310                 315                 320

Val Arg Phe Val Lys Gly Gly Ala Gly Ser Ala Tyr Gly Gly Asn Val
                325                 330                 335

Glu Val Lys Val Val Asp Pro Ser Ala Asn Pro Tyr Leu Ala Ser Ala
            340                 345                 350

Ala Ile Leu Gly Leu Ala Leu Asp Gly Met Lys Thr Lys Ala Val Leu
                355                 360                 365

Pro Ser Glu Thr Thr Val Asp Pro Thr Gln Leu Ser Asp Val Asp Arg
            370                 375                 380

Asp Arg Ala Gly Ile Leu Arg Leu Ala Ala Asp Gln Ala Asp Ala Ile
385                 390                 395                 400

Ala Val Leu Asp Ser Ser Lys Leu Leu Arg Cys Ile Leu Gly Asp Pro
                405                 410                 415

Val Val Asp Ala Val Val Ala Val Arg Gln Leu Glu His Glu Arg Tyr
            420                 425                 430
```

```
Gly Asp Leu Asp Pro Ala Gln Leu Ala Asp Lys Phe Arg Met Ala Trp
        435                 440                 445

Ser Val
    450

<210> SEQ ID NO 13
<211> LENGTH: 1374
<212> TYPE: DNA
<213> ORGANISM: Mycobacterium tuberculosis
<220> FEATURE:
<221> NAME/KEY: CDS
<222> LOCATION: (1)..(1374)
<223> OTHER INFORMATION: Sequence is identical to complement of
      nucleotides 3104-4477of GenBank entry GB:MTV003 [AL008883]
      Sequence is identical to complement of nucleotides 3138-4511
      of GenBank entry GB:AE007117

<400> SEQUENCE: 13 gtg acc ggc ccc ggt tcg ccg ccg ttg gcg tgg acc gag ttg gag cga      48
Met Thr Gly Pro Gly Ser Pro Pro Leu Ala Trp Thr Glu Leu Glu Arg
1               5                   10                  15 ctg gtc gcg gcc ggt gac gtc gac acc gtc atc gtc gcg ttc acc gac      96
Leu Val Ala Ala Gly Asp Val Asp Thr Val Ile Val Ala Phe Thr Asp
            20                  25                  30 atg cag ggc cgg ctg gcc ggc aaa cgg ata tcg ggc cgg cat ttc gtc     144
Met Gln Gly Arg Leu Ala Gly Lys Arg Ile Ser Gly Arg His Phe Val
        35                  40                  45 gac gac ata gcc acc cgc ggc gtc gag tgc tgc agt tat ctg ctg gcc     192
Asp Asp Ile Ala Thr Arg Gly Val Glu Cys Cys Ser Tyr Leu Leu Ala
    50                  55                  60 gtg gac gtc gac ctg aac acg gtg ccc ggc tat gcg atg gcc agt tgg     240
Val Asp Val Asp Leu Asn Thr Val Pro Gly Tyr Ala Met Ala Ser Trp
65                  70                  75                  80 gac acc ggc tac ggc gat atg gtg atg acg ccg gac ttg tcc act ctg     288
Asp Thr Gly Tyr Gly Asp Met Val Met Thr Pro Asp Leu Ser Thr Leu
                85                  90                  95 cgg ctg att cct tgg cta ccg gga acg gcg ctg gtg atc gcc gac ctg     336
Arg Leu Ile Pro Trp Leu Pro Gly Thr Ala Leu Val Ile Ala Asp Leu
            100                 105                 110 gtc tgg gcc gac ggc agc gag gtc gcc gtc tcg ccg cgc agc att ctg     384
Val Trp Ala Asp Gly Ser Glu Val Ala Val Ser Pro Arg Ser Ile Leu
        115                 120                 125 cgc cgt cag ctc gat cgg ctc aag gcg cgc gga ctg gtc gcc gat gtg     432
Arg Arg Gln Leu Asp Arg Leu Lys Ala Arg Gly Leu Val Ala Asp Val
    130                 135                 140 gcc acc gag ctg gag ttc atc gtg ttc gac cag ccg tat cgc cag gca     480
Ala Thr Glu Leu Glu Phe Ile Val Phe Asp Gln Pro Tyr Arg Gln Ala
145                 150                 155                 160 tgg gcc agc ggg tat cgc ggg ctg acc ccg gcc agc gac tac aac atc     528
Trp Ala Ser Gly Tyr Arg Gly Leu Thr Pro Ala Ser Asp Tyr Asn Ile
                165                 170                 175 gac tac gcg ata ttg gca tcc tcg cgg atg gag ccg ttg ctg cgc gac     576
Asp Tyr Ala Ile Leu Ala Ser Ser Arg Met Glu Pro Leu Leu Arg Asp
            180                 185                 190 atc cgg ttg ggt atg gcc ggt gcg ggt ctg cga ttc gag gcg gtc aaa     624
Ile Arg Leu Gly Met Ala Gly Ala Gly Leu Arg Phe Glu Ala Val Lys
        195                 200                 205 ggc gaa tgc aac atg ggc cag cag gag atc ggg ttt cgt tac gac gag     672
Gly Glu Cys Asn Met Gly Gln Gln Glu Ile Gly Phe Arg Tyr Asp Glu
    210                 215                 220 gcg ctg gtc acc tgc gac aac cat gcg atc tac aag aac ggc gcc aag     720
Ala Leu Val Thr Cys Asp Asn His Ala Ile Tyr Lys Asn Gly Ala Lys
```

```
gaa atc gcc gac cag cac ggc aag agc cta acg ttc atg gcg aaa tac    768
Glu Ile Ala Asp Gln His Gly Lys Ser Leu Thr Phe Met Ala Lys Tyr
            245                 250                 255 gat gaa cgc gaa ggt aat agc tgt cac atc cat gtc tcg ctg cgt ggc    816
Asp Glu Arg Glu Gly Asn Ser Cys His Ile His Val Ser Leu Arg Gly
        260                 265                 270 acg gat ggc tcc gcg gtg ttt gcc gac agt aac ggg ccg cac ggc atg    864
Thr Asp Gly Ser Ala Val Phe Ala Asp Ser Asn Gly Pro His Gly Met
    275                 280                 285 tcg tcg atg ttc cgc agc ttc gtc gcc ggc cag ttg gcc acg ttg cgc    912
Ser Ser Met Phe Arg Ser Phe Val Ala Gly Gln Leu Ala Thr Leu Arg
290                 295                 300 gaa ttc acg ctg tgc tat gcg ccg acc att aac tcc tac aag cga ttt    960
Glu Phe Thr Leu Cys Tyr Ala Pro Thr Ile Asn Ser Tyr Lys Arg Phe
305                 310                 315                 320 gcc gat agc agt ttc gcg ccg acg gcg ctg gct tgg ggg ctg gac aat   1008
Ala Asp Ser Ser Phe Ala Pro Thr Ala Leu Ala Trp Gly Leu Asp Asn
                325                 330                 335 cgc acc tgc gcc ctg cgg gtg gtt ggc cac ggg caa aac atc cgg gtc   1056
Arg Thr Cys Ala Leu Arg Val Val Gly His Gly Gln Asn Ile Arg Val
            340                 345                 350 gaa tgc cgg gtt ccc ggc ggt gat gtc aac cag tac ctg gcg gtg gcg   1104
Glu Cys Arg Val Pro Gly Gly Asp Val Asn Gln Tyr Leu Ala Val Ala
        355                 360                 365 gct ctc att gct gga ggg ttg tac ggt atc gag cgg ggc ctt cag ctg   1152
Ala Leu Ile Ala Gly Gly Leu Tyr Gly Ile Glu Arg Gly Leu Gln Leu
    370                 375                 380 ccc gag ccc tgt gtc ggc aac gcc tac caa ggc gcc gat gtc gaa cgg   1200
Pro Glu Pro Cys Val Gly Asn Ala Tyr Gln Gly Ala Asp Val Glu Arg
385                 390                 395                 400 ctg ccg gtt acg ctg gcc gac gcc gcg gtg ctg ttc gag gat tct gcg   1248
Leu Pro Val Thr Leu Ala Asp Ala Ala Val Leu Phe Glu Asp Ser Ala
                405                 410                 415 ctg gtg cgc gag gcg ttc ggc gag gat gtt gtc gcg cac tac ctg aac   1296
Leu Val Arg Glu Ala Phe Gly Glu Asp Val Val Ala His Tyr Leu Asn
            420                 425                 430 aac gcg cgt gtg gag ctg gcg gcg ttc aac gcg gcg gtc acc gat tgg   1344
Asn Ala Arg Val Glu Leu Ala Ala Phe Asn Ala Ala Val Thr Asp Trp
        435                 440                 445 gag agg ata cgt gga ttt gag cgc ctc tag                            1374
Glu Arg Ile Arg Gly Phe Glu Arg Leu
    450                 455
```

<210> SEQ ID NO 14
<211> LENGTH: 457
<212> TYPE: PRT
<213> ORGANISM: Mycobacterium tuberculosis
<220> FEATURE:
<221> NAME/KEY:
<222> LOCATION:
<223> OTHER INFORMATION: Sequence is identical to PIR entry PIR:F70885

<400> SEQUENCE: 14

```
Met Thr Gly Pro Gly Ser Pro Pro Leu Ala Trp Thr Glu Leu Glu Arg
1               5                   10                  15

Leu Val Ala Ala Gly Asp Val Asp Thr Val Ile Val Ala Phe Thr Asp
            20                  25                  30

Met Gln Gly Arg Leu Ala Gly Lys Arg Ile Ser Gly Arg His Phe Val
        35                  40                  45
```

-continued

```
Asp Asp Ile Ala Thr Arg Gly Val Glu Cys Cys Ser Tyr Leu Leu Ala
 50              55                  60

Val Asp Val Asp Leu Asn Thr Val Pro Gly Tyr Ala Met Ala Ser Trp
 65                  70                  75                  80

Asp Thr Gly Tyr Gly Asp Met Val Met Thr Pro Asp Leu Ser Thr Leu
                 85                  90                  95

Arg Leu Ile Pro Trp Leu Pro Gly Thr Ala Leu Val Ile Ala Asp Leu
            100                 105                 110

Val Trp Ala Asp Gly Ser Glu Val Ala Val Ser Pro Arg Ser Ile Leu
        115                 120                 125

Arg Arg Gln Leu Asp Arg Leu Lys Ala Arg Gly Leu Val Ala Asp Val
130                 135                 140

Ala Thr Glu Leu Glu Phe Ile Val Phe Asp Gln Pro Tyr Arg Gln Ala
145                 150                 155                 160

Trp Ala Ser Gly Tyr Arg Gly Leu Thr Pro Ala Ser Asp Tyr Asn Ile
                165                 170                 175

Asp Tyr Ala Ile Leu Ala Ser Ser Arg Met Glu Pro Leu Leu Arg Asp
            180                 185                 190

Ile Arg Leu Gly Met Ala Gly Ala Gly Leu Arg Phe Glu Ala Val Lys
        195                 200                 205

Gly Glu Cys Asn Met Gly Gln Gln Glu Ile Gly Phe Arg Tyr Asp Glu
210                 215                 220

Ala Leu Val Thr Cys Asp Asn His Ala Ile Tyr Lys Asn Gly Ala Lys
225                 230                 235                 240

Glu Ile Ala Asp Gln His Gly Lys Ser Leu Thr Phe Met Ala Lys Tyr
                245                 250                 255

Asp Glu Arg Glu Gly Asn Ser Cys His Ile His Val Ser Leu Arg Gly
            260                 265                 270

Thr Asp Gly Ser Ala Val Phe Ala Asp Ser Asn Gly Pro His Gly Met
        275                 280                 285

Ser Ser Met Phe Arg Ser Phe Val Ala Gly Gln Leu Ala Thr Leu Arg
290                 295                 300

Glu Phe Thr Leu Cys Tyr Ala Pro Thr Ile Asn Ser Tyr Lys Arg Phe
305                 310                 315                 320

Ala Asp Ser Ser Phe Ala Pro Thr Ala Leu Ala Trp Gly Leu Asp Asn
                325                 330                 335

Arg Thr Cys Ala Leu Arg Val Val Gly His Gly Gln Asn Ile Arg Val
            340                 345                 350

Glu Cys Arg Val Pro Gly Gly Asp Val Asn Gln Tyr Leu Ala Val Ala
        355                 360                 365

Ala Leu Ile Ala Gly Gly Leu Tyr Gly Ile Glu Arg Gly Leu Gln Leu
370                 375                 380

Pro Glu Pro Cys Val Gly Asn Ala Tyr Gln Gly Ala Asp Val Glu Arg
385                 390                 395                 400

Leu Pro Val Thr Leu Ala Asp Ala Ala Val Leu Phe Glu Asp Ser Ala
                405                 410                 415

Leu Val Arg Glu Ala Phe Gly Glu Asp Val Val Ala His Tyr Leu Asn
            420                 425                 430

Asn Ala Arg Val Glu Leu Ala Ala Phe Asn Ala Ala Val Thr Asp Trp
        435                 440                 445

Glu Arg Ile Arg Gly Phe Glu Arg Leu
450                 455
```